United States Patent [19]
Okazaki et al.

[11] Patent Number: 6,100,362
[45] Date of Patent: Aug. 8, 2000

[54] SULFUR-CONTAINING URETHANE-BASED RESIN AND COMPOSITION AND PROCESS FOR PRODUCING THE RESIN

[75] Inventors: Koju Okazaki; Yoshinobu Kanemura; Teruyuki Nagata, all of Fukuoka-ken, Japan

[73] Assignee: Mitsui Chemicals, Inc., Tokyo, Japan

[21] Appl. No.: 08/946,347

[22] Filed: Oct. 7, 1997

Related U.S. Application Data

[62] Division of application No. 08/753,436, Nov. 25, 1996, Pat. No. 5,837,797, which is a division of application No. 08/373,038, Jan. 17, 1995, Pat. No. 5,608,115.

[30] Foreign Application Priority Data

Jan. 26, 1994 [JP] Japan ................................. 6-006792

[51] Int. Cl.⁷ ............................ C08G 18/38; C08G 18/52
[52] U.S. Cl. ................................................ 528/76; 528/85
[58] Field of Search ........................................ 528/76, 85

[56] References Cited

U.S. PATENT DOCUMENTS 5,087,758   2/1992   Kanemura et al. .
5,283,312   2/1994   Kanemura et al. .

FOREIGN PATENT DOCUMENTS 0528590    2/1993    European Pat. Off. .
0378895    7/1993    European Pat. Off. .
0665219    8/1995    European Pat. Off. .
0713105   11/1995    European Pat. Off. .
6-065190   3/1994    Japan .
6-116337   4/1994    Japan .

*Primary Examiner*—Patricia A. Short
*Attorney, Agent, or Firm*—Burns, Doane, Swecker & Mathis, L.L.P.

[57] ABSTRACT

A polythiol having four or more functional groups, a process for producing the polythiol comprising reacting thiourea with a specific compound, a sulfur-containing urethane-based resin prepared from the polythiol and a lens made of the resin. The resin has a high refractive index, and low dispersion of refractive index, is lightweight, colorless and transparent, has no optical distortion, and has excellent characteristics in weatherability, dye-affinity, heat resistance, impact resistance and machinability.

19 Claims, 1 Drawing Sheet

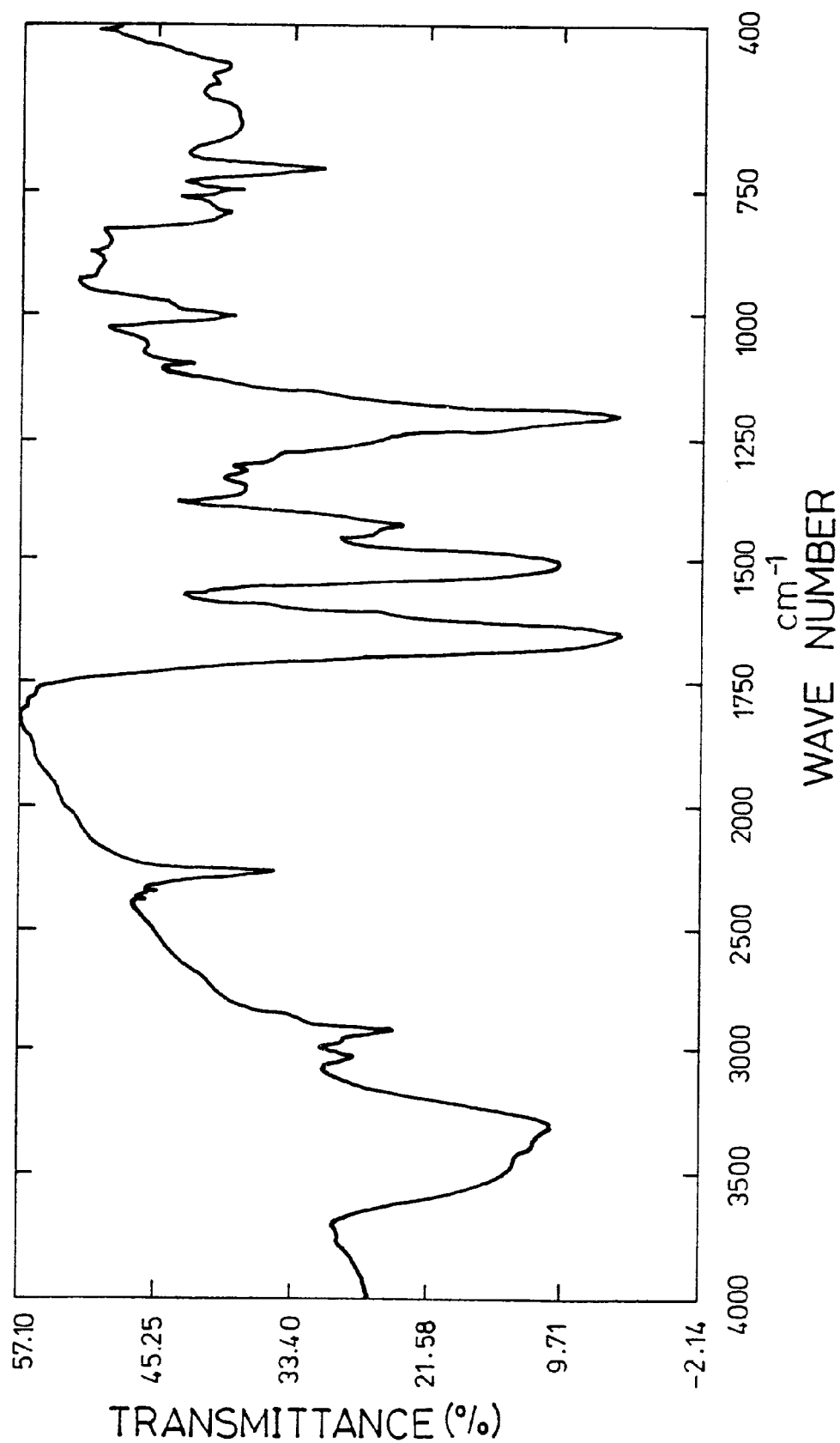

SULFUR-CONTAINING URETHANE-BASED RESIN AND COMPOSITION AND PROCESS FOR PRODUCING THE RESIN

This application is a divisional of application Ser. No. 08/753,436, filed Nov. 25, 1996, now U.S. Pat. No. 5,837,797, which is a divisional of application Ser. No. 08/373,083, filed on Jan. 17, 1995, now U.S. Pat. No. 5,608,115.

BACKGROUND OF THE INVENTION

1. Field of the Invention

The present invention relates to a novel polythiol and a process for producing the same, a sulfur-containing urethane-based resin prepared from the polythiol and a lens made of the resin.

The polythiol of the present invention finds wide applications in, for example, raw materials for synthetic resins, crosslinking agents, epoxy resin curing agents, vulcanizing agents, polymerization regulators, metal complex forming agents and biochemical lubricating oil additives in addition to the above-mentioned raw material for the sulfur-containing urethane-based resin.

2. Description of the Prior Art

There have hitherto been used, for example, polythiols formed by the esterification of polyols such as pentaerythritol and trimethylolpropane with mercaptocarboxylic acids such as mercaptopropionic acid and thioglycolic acid for the aforementioned applications. Plastic lenses are lighter in weight, less fragile and easier to dye than inorganic lenses, and hence have been increasingly popular for use as optical elements such as eyeglass lenses and camera lenses.

Resins formed by subjecting diethylene glycol bis (allylcarbonate) (hereinafter referred to as DAC) to radical polymerization have widely been used to date for optical elements.

The resins have a variety of features such as excellent impact resistance, light weight, prominent dye-affinity and superb machinability including cutting ability and polishing ability.

However, lenses made from DAC have a smaller refractive index ($n_D$=1.50) than inorganic lenses ($n_D$=1.52). In order to obtain equivalent optical properties to glass lenses, it is necessary to increase the center thickness, peripheral thickness and curvature of the lens and hence the lens as a whole becomes unavoidably thick. Therefore, lens-making resins with higher refractive index are desired. As one of the lens-making resins giving higher refractive index, there has been known a polyurethane-based resin for making plastic lenses, which is obtained by reacting an isocyanate compound with a hydroxyl compound such as diethylene glycol (Japanese Patent Laid-Open No. 136601/1982), with a halogen-containing hydroxyl compound such as tetrabromobisphenol-A (Japanese Patent Laid-Open No. 164615/1983), and with a diphenyl-sulfide-linkage-containing hydroxyl compound (Japanese Patent Laid-Open No. 194401/1985).

Although lenses made of these prior art resins have improved refractive indices over lenses made from DAC, their refractive indices are still insufficient. Moreover, these resins have such defects as poor weather-ability and impact resistance or large specific gravity due to the presence of a number of halogen atoms or aromatic rings in the molecule for the purpose of improving their refractive indices.

The present inventors have found earlier that an S-alkyl thiocarbamate resin obtained by reacting pentaerythritol tetrakis(2-mercaptoacetate) (hereinafter referred to as PETG) with xylylene diisocyanate (hereinafter referred to as XDi) has a high refractive index, is colorless and transparent and has excellent mechanical properties and machinability (Japanese Patent Laid-Open No. 199016/1985).

However, even the S-alkyl thiocarbamate resin had such defects as insufficient refractive index, thick peripheral thickness and reduced fashonability when the lens was used for strong sizing of visual acuity.

In consequence, the present inventors have made further examinations to find out a novel compound, 1,2-bis(2-mercaptoethylthio)-3-propanethiol (hereinafter referred to as GST), and found that resins prepared from GST have higher refractive indices than the resins from PETG and are colorless, transparent and excellent in dye-affinity so that they are distinguished as plastic lens materials (Japanese Patent Laid-Open No. 270859/1990).

However, the resin formed by reacting GST with XDi, which is most generally used as a raw material of a plastic lens, has a glass transition temperature of 98° C., and therefore the lens made of the resin is deformed at a common dyeing temperature for plastic lenses of 90 to 95° C., which is close to the critical heat-resistant temperature of the resin. Hence, the lens needs reheating for its restoration, but this is troublesome.

Consequently, the inventors have made further examinations, and found 2-mercaptoethylthio-1,3-propanedithiol (hereinafter referred to as GMT) which gives heat-resistant resins that are not deformed even at the common dyeing temperature (90–95° C.) as well as have equivalent optical properties to resins made from GST (Japanese Patent Laid-Open No. 208950/1993).

However, GMT is a trifunctional thiol and hence, when it is combined with a bifunctional isocyanate to produce a resin, a crosslinked structure of the resin is formed at the final stage of the polymerization so that viscosity increase during the polymerization is slow and resin additives such as a plasticizer usually bleed into the molding from a resin-made gasket used for molding plastic lenses, thus impairing the transparency of the molding. To solve this problem, the polymerization is carried out at a low temperature for a long time and then completed at a high temperature by way of example. This case however gives a prolonged polymerization time and reduced productivity.

SUMMARY OF THE INVENTION

An object of the present invention is to provide a polythiol compound which provides with improved productivity, a heat-resistant resin that has equivalent optical properties compared to one prepared from GST or GMT and is not deformed at the ordinary dyeing temperature (90–95° C.).

With such situations in view, the inventors have made examinations to meet the above-described requirements and, as a result, found that a novel polythiol with four or more functional groups which has the specific structure of the present invention can solve the foregoing problems, leading to completion of the present invention.

The present invention provides:

(I) a polythiol having four or more functional groups represented by any of the following formula (1):

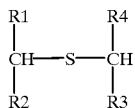  (1)

wherein R1, R2, R3 and R4 are each selected from the group consisting of H, —CH$_2$SH, CH$_2$SCH$_2$CH$_2$SH,

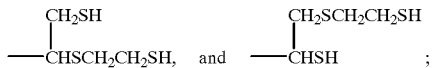

provided that where any one of R1, R2, R3 and R4 is H, at least one of other three radicals represents

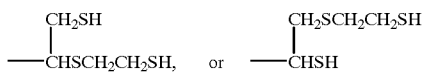

where any two of R1, R2, R3 and R4 are H, two of others are independently selected from

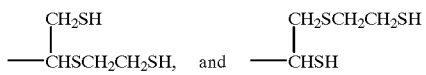

and any three or all of R1, R2, R3 and R4 are not H simultaneously;
formula (2):

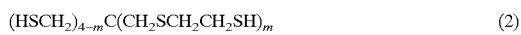  (2)

wherein m denotes an integer of 1 to 3; and formula (3):

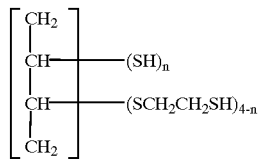  (3)

wherein n denotes an integer of 0 to 3;
(II) a process for producing the polythiol having four or more functional groups according to claim 1, which comprises the steps of the preparation of isothiouronium salt by reacting a compound selected from the group consisting of the following formulae (4), (5) and (6) with thiourea:

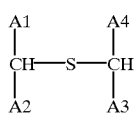  (4)

wherein A1, A2, A3 and A4 are independently selected from the group consisting of H, —CH$_2$X, —CH$_2$SCH$_2$CH$_2$X,

provided that where any one of A1, A2, A3 and A4 is H, at least one of other three radicals is

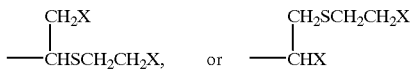

where any two of A1, A2, A3 and A4 are H, two of others are independently selected from

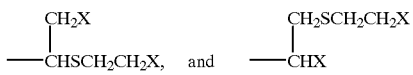

and any three or all of A1, A2, A3 and A4 are not H simultaneously, and Xs denote each an OH group, a chlorine atom, a bromine atom, an iodine atom, a methanesulfonyl group, a benzenesulfonyl group or a p-toluenesulfonyl group;

  (5)

wherein m is an integer of 1 to 3 and Xs have the same meaning as defined above; and

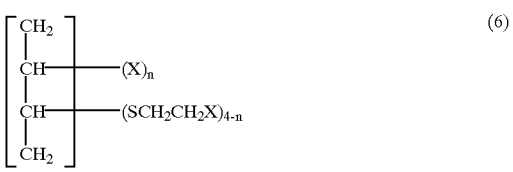  (6)

wherein n is a integer of 0 to 3 and X is as defined as above, and of hydrolyzing the thus obtained isothiouronium salt with a based;
(III) a sulfur-containing urethane-based resin composition comprising the polythiol having 4 or more functional groups of item (I) and at least one isocyanate selected from polyisocyanate compounds, polyisothiocyanate compounds and isocyanato-containing polyisothiocyanate compounds;
(IV) the composition of item (III) wherein the mixing proportion of the isocyanate to the polythiol is from 0.5 to 3.0 in terms of the molar ratio of the functional groups (NCO+NCS)/SH;
(V) a process for producing a sulfur-containing urethane-based resin which comprises curing the composition of item (III) by heating;
(VI) a sulfur-containing urethane-based resin obtained by the process of item (V);
(VII) the process of item (V) wherein the mixing proportion of the isocyanate to the polythiol is from 0.5 to 3.0 in terms of the molar ratio of the functional groups (NCO+NCS)/SH;
(VIII) a sulfur-containing urethane-based resin obtained by the process of item (VII);
(IX) a process for preparing a sulfur-containing urethane-based plastic lens which comprises polymerizing the composition of item (III) in a mold and then releasing the molding from the mold;
(X) a sulfur-containing urethane-based plastic lens prepared by the process of item (IX);
(XI) the process of item (IX) wherein the mixing proportion of the isocyanate to the polythiol is from 0.5 to 3.0 in terms of the molar ratio of the functional groups (NCO+NCS)/SH; and
(XII) a sulfur-containing urethane-based plastic lens prepared by the process of item (XI).

BRIEF DESCRIPTION OF THE DRAWING

FIG. 1 shows an infrared absorption spectrum of a plastic lens prepared in accordance with the present invention.

DETAILED DESCRIPTION OF THE INVENTION

The polythiol having four or more functional groups represented by formula (1) includes the following compounds by way of example.

(where R1=R2=R3=R4)

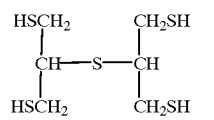
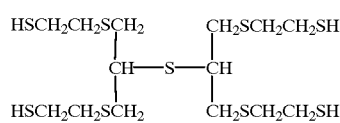
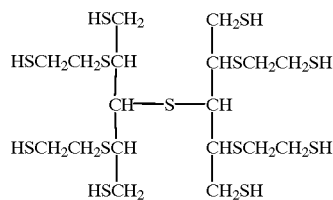
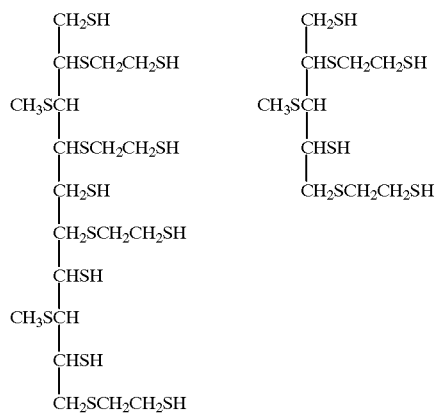

where R2=R3=H

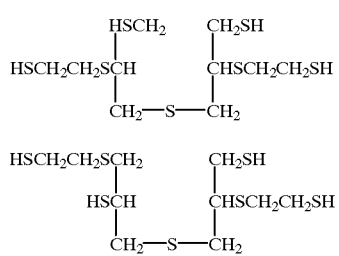
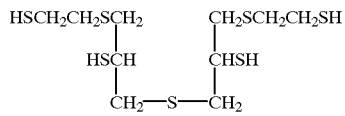

where any one of R1 through R4 is H:

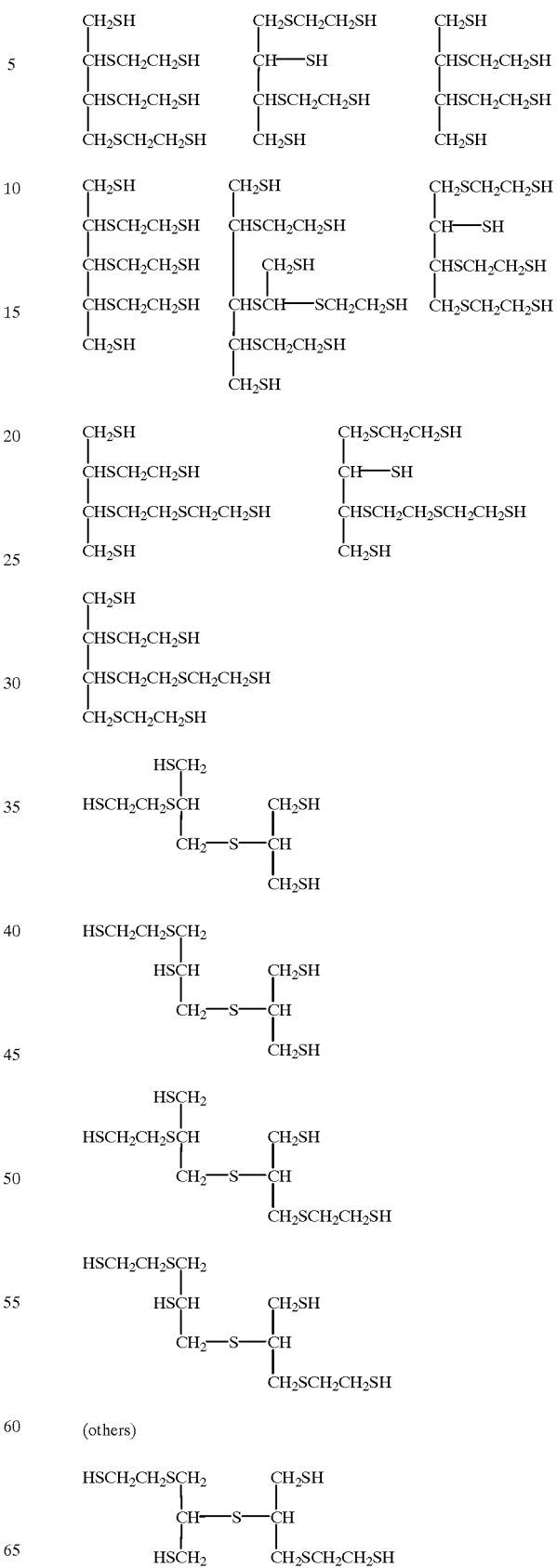

(others)

-continued

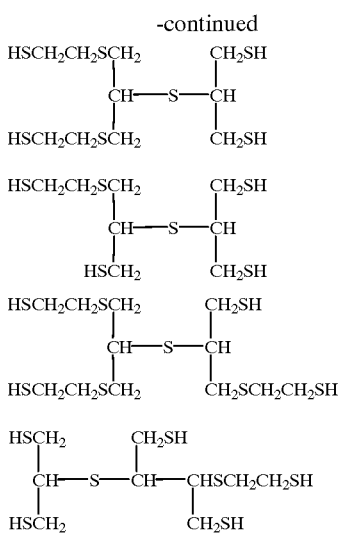

The polythiols represented by formula (2) are exemplified as follows:

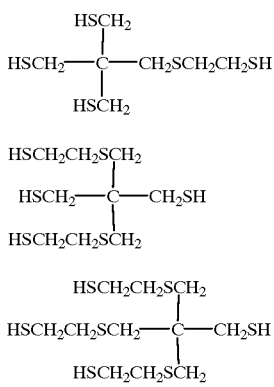

The polythiols represented by formula (3) are exemplified as follows:

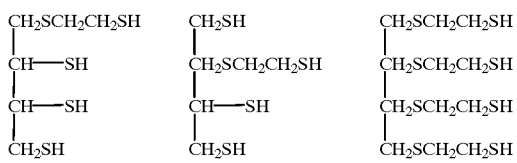

The sulfur-containing urethane-based, resin prepared from the polythiol having four or more functional groups according to the present invention has solved the above-mentioned problems, and therefore it is colorless and transparent, shows no optical distortion, has a high refractive index and low dispersion of refractive index (a high Abbe's number), is of a low specific gravity, is excellent in impact strength, dye-affinity, heat resistance and machinability, so that it has satisfactory properties as a resin for plastic lenses.

The polythiol having four or more functional groups according to the present invention can be prepared by any known procedure for synthesizing polythiols as described in literature (e.g. The Chemistry of the Thiol Group), but it is preferable from the aspect of coloration of the product to produce it by the isothiouronium salt process which comprises reacting a compound of formula (4), (5) or (6) with thiourea to form an isothiouronium salt and hydrolyzing the salt.

The polyols, polyhalogen compounds and hydroxylated halides of formulae (4), (5), and (6) can be obtained, for example, by reacting an organic low-molecular epoxy compound such as an epihalohydrin and butadiene epoxide, a glycerol derivative such as 2-chloro-1,3-propanediol, thioglycerol and tribromopropane or an organic low-molecular halide such as 1,2,3,4-tetrabromobutane and 1,2,3,4,5-pentachloropentane with an ethylene derivative such as 2-mercaptoethanol and ethylene oxide and a sulfide such as sodium hydrogensulfide, sodium sulfide, potassium sulfide and hydrogen sulfide.

The eliminable-group-containing compounds of formulae (4), (5) and (6) can also be obtained by replacing the OH group or groups of the corresponding polyol or hydroxylated halide of formula (4), (5) or (6) with the eliminable group or groups.

To replace the OH group or groups with the eliminatable group or groups, it is possible to use reactions for introducing the eliminatable group or groups into a common alcohol. For example, it is mentioned to react an alcohol with a hydrogen halide such as hydrogen chloride, hydrobromic acid and hydroiodic acid, to use in the reactions the hydrogen halide and a metal halide such as zinc chloride, to use an alkali metal salt such as potassium iodide and sodium bromide and an acid such as sulfuric acid and phosphoric acid, to use a halogen and phosphorus, and to use thionyl chloride, phosphorus tribromide, phosphorus pentachloride, methanesulfonyl chloride, benzenesulfonyl chloride, p-toluenesulfonyl chloride, or the like.

In the next step of the isothiouronium salt reaction, a polyfunctional compound of formula (4), (5) or (6) is reacted with generally four equivalents or more, preferably four to eight equivalents of thiourea based on the compound. Where the compound contains an OH group or groups, the reaction is effected in the presence of generally one equivalent or more, preferably one to five equivalents of a mineral acid based on the OH group or groups. The mineral acid includes hydrochloric acid, hydrobromic acid, hydroiodic acid, sulfuric acid, phosphoric acid, etc., but hydrochloric acid or hydrobromic acid is preferred from the viewpoint of reaction rate, economical efficiency and coloring of the product.

The subsequent hydrolysis is carried out by adding to the foregoing reaction liquid generally four equivalents or more, preferably four to twenty equivalents of an inorganic base such as sodium hydroxide, potassium hydroxide, sodium carbonate, sodium acetate and potassium phosphate or an organic base such as ammonia, triethylamine and hydrazine based on the polyfunctional compound of formula (4), (5) or (6) to obtain a desired polythiol having four or more functional groups.

No limitations are imposed on the reaction temperatures up to the obtainment of the polythiol having four or more functional groups, because they vary with the processes and catalysts employed. However, the reaction for obtaining the compound of formula (4), (5) or (6), the isothiouronium salt reaction and the hydrolysis are all carried out preferably at 0 to 200° C., more preferably at 20 to 120° C. by way of example.

Similarly, the reaction pressure is not limited and therefore reduced, atmospheric or elevated pressure may be employed. However, atmospheric pressure is preferred because of cost and reduction of equipment and facility.

The polythiol having four or more functional groups of formula (1), (2) or (3) obtained in the above manner can be purified by common procedures including acid washing, base washing, water washing, concentration, filtration, etc. and can also be distilled, if necessary, after it has been extracted with an organic solvent such as toluene. The preparation of the polythiol having four or more functional groups can be effected in the air, but it is preferable to carry out the preparation as a whole in a stream of nitrogen in order to make assurance in the prevention of oxidation and coloring of the raw materials and the product.

The synthesis of the polythiol having four or more functional groups according to the present invention is illustrated below. For example, where R1=R3=H and R2=R4=

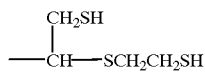

in formula (1), the polythiol can be synthesized in the following manner:

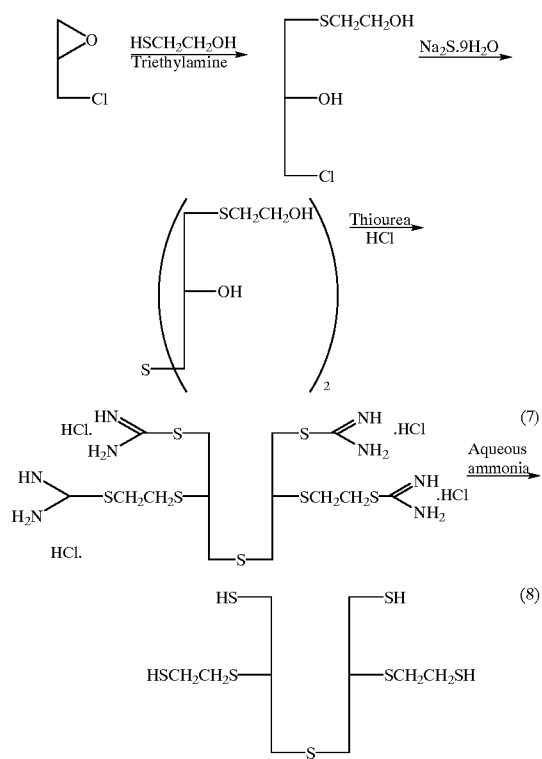

Namely, epichlorohydrin is reacted with 2-mercaptoethanol in the presence of triethylamine to obtain a diol, which is further reacted with sodium sulfide to obtain a tetraol.

The tetraol is reacted with thiourea in hydrochloric acid to obtain an isothiouronium salt. At this moment, rearrangement takes place to form an isomer mixture tetraisothiouronium salt containing that of formula (7).

Finally, aqueous ammonia is added to the reaction liquid to hydrolyze the salt so as to obtain an isomer mixture polythiol containing the desired polythiol of formula (8).

As another method, where R1=R2=R3=R4=—CH$_2$SH in formula (1) by way of example, the polythiol can be synthesized also in the following manner:

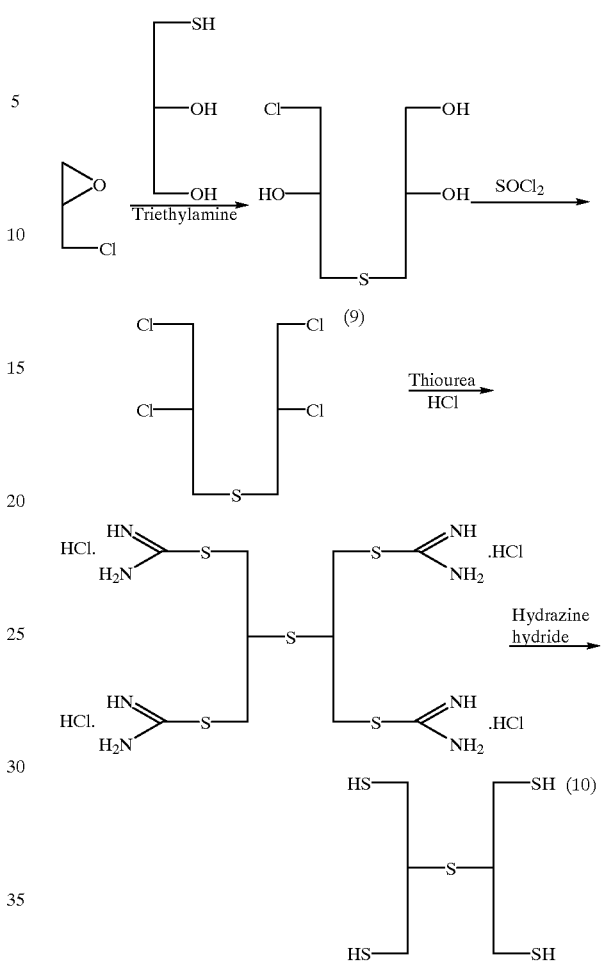

Namely, epichlorohydrin is reacted with thioglycerol in the presence of triethylamine to obtain a triol.

Then, the reaction liquid is reacted with thionyl chloride to obtain a chlorinated derivative. At this moment, rearrangement takes place partially to form an isomer mixture tetrachloride-containing that of formula (9). Then, the isomer mixture tetrachloride is reacted with thiourea to form an isothiouronium salt, to which hydrazine hydrate is added to hydrolyze the salt to obtain the desired polythiol of formula (10). The rearrangement is completed by the isothiouronium salt reaction.

The sulfur-containing urethane-based resin of the present invention is obtained by reacting a polythiol of formulae (1) through (3) with at least one isocyanate selected from polyisocyanate compounds, polyisothiocyanate compounds and isocyanato-containing polyisothiocyanates.

Active hydrogen compounds such as hydroxyl compounds, mercapto compounds other than those of formulae (1) to (3) and hydroxylated mercapto compounds or monoisocyanates such as monoisocyanate compounds and monoisothiocyanate compounds may be added to the reaction system in order to modify the resin.

The polyisocyanate compound used as a raw material for the sulfur-containing urethane-based resin in the present invention includes, for example, aliphatic polyisocyanates such as ethylene diisocyanate, trimethylene diisocyanate, tetramethylene diisocyanate, hexamethylene diisocyanate, octamethylene diisocyanate, nonamethylene diisocyanate, 2,2'-dimethylpentane diisocyanate, 2,2,4-trimethylhexane diisocyanate, decamethylene diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanato-4-(isocyanatomethyl)octane, 2,5,7-trimethyl-1,8-diisocyanato-5-(isocyanatomethyl)octane, bis(isocyanatoethyl)-carbonate, bis(isocyanatoethyl)ether, 1,4-butyleneglycol-dipropylether-ω,ω'-diisocyanate, lysinediisocyanate methyl ester, lysinetriisocyanate, 2-isocyanatoethyl-2,6-diisocyanatohexanoate, 2-isocyanatopropyl-2,6-diisocyanatohexanoate, xylylene diisocyanate, bis(isocyanatoethyl)benzene, bis-(isocyanatopropyl)benzene, α,α,α',α'-tetramethylxylylene diisocyanate, bis(isocyanatobutyl)benzene, bis(isocyanatomethyl)naphthalene, bis(isocyanatomethyl) diphenyl ether, bis(isocyanatoethyl)phthalate, mesitylene triisocyanate and 2,6-di(isocyanatomethyl)furan; alicyclic polyisocyanates such as isophorone diisocyanate, bis(isocyanatomethyl)cyclohexane, dicyclohexylmethane diisocyanate, cyclohexane diisocyanate, methylcyclohexane diisocyanate, dicyclohexyldimethylmethane diisocyanate, 2,2'-dimethyldicyclohexylmethane diisocyanate, bis(4-isocyanato-n-butylidene)pentaerythritol, dimeric acid diisocyanate, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-3-(3-isocyanatopropyl)-6-(2-isocyanatoethyl)-bicyclo[2.1.1]-heptane, 2-isocyanatomethyl-2-(3-isocyanatopropyl)-5-(2-isocyanatoethyl)-bicyclo[2.2.1]-heptane, and 2-isocyanatomethyl-2-(3-isocyanatopropyl)-6-(2-isocyanatoethyl)-bicyclo[2.2.1]-heptane;

aromatic polyisocyanates such as phenylene diisocyanate, tolylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, naphthalene diisocyanate, methylnaphthalene diisocyanate, biphenyl diisocyanate, tolidine diisocyanate, 4,4'-diphenylmethane diisocyanate, 3,3'-dimethyl-diphenylmethane-4,4'-diisocyanate, bibenzyl-4,4'-diisocyanate, bis(isocyanatophenyl)ethylene, 3,3'-dimethoxybiphenyl-4,4'-diisocyanate, triphenylmethane triisocyanate, polymeric MDI, naphthalene triisocyanate, diphenylmethane-2,4,4'-triisocyanate,3-methyldiphenylmethane-4,6,4'-triisocyanate, 4-methyldiphenyl-methane-3,5,2',4',6'-pentaisocyanate, phenylisocyanatomethyl isocyanate, phenylisocyanatoethyl isocyanate, tetrahydronaphthylene diisocyanate, hexahydrobenzene diisocyanate, hexahydrodiphenylmethane-4,4'-diisocyanate, diphenylether diisocyanate, ethyleneglycol-diphenylether diisocyanate, 1,3-propyleneglycoldiphenylether diisocyanate, benzophenone diisocyanate, diethyleneglycol-diphenylether diisocyanate, dibenzofuran diisocyanate, carbazole diisocyanate, ethylcarbazole diisocyanate and dichlorocarbazole diisocyanate;

sulfur-containing aliphatic polyisocyanates such as thiodiethyl diisocyanate, thiodipropyl diisocyanate, thiodihexyl diisocyanate, dimethylsulfone diisocyanate, dithiodimethyl diisocyanate, dithiodiethyl diisocyanate, dithiodipropyl diisocyanate and dicyclohexylsulfide-4,4'-diisocyanate;

aromatic sulfide-type polyisocyanates such as diphenylsulfide-2,4'-diisocyanate, diphenylsulfide-4,4'-diisocyanate, 3,3'-dimethoxy-4,4'-diisocyanatodibenzyl thioether, bis(4-isocyanatomethylbenzene)-sulfide and 4,4'-methoxybenzene-thioethyleneglycol-3,3'-diisocyanate;

aromatic disulfide-type polyisocyanates such as dipenyldisulfide-4,4'-diisocyanate, 2,2'-dimethyldiphenyl-disulfide-5,5'-diisocyanate, 3,3'-dimethyldiphenyldisulfide-5,5'-diisocyanate, 3,3'-dimethyldiphenyldisulfide-6,6'-diisocyanate, 4,4'-dimethyldiphenyldisulfide-5,5'-diisocyanate, 3,3'-dimethoxydiphenyldisulfide-4,4'-diisocyanate and 4,4'-dimethoxydiphenyldisulfide-3,3'-diisocyanate;

aromatic sulfone-type polyisocyanates such as diphenylsulfone-4,4'-diisocyanate, diphenylsulfone-3,3'-diisocyanate, benzidinesulfone-4,4'-diusocyanate, diphenylmethanesulfone-4,4'-diisocyanate, 4-methyldiphenylmethanesulfone-2,4'-diisocyanate, 4,4'-dimethoxydiphenylsulfone-3,3'-diisocyanate, 3,3'-dimethoxy-4,4'-diisocyanatodibenzylsulfone, 4,4'-dimethyldiphenylsulfone-3,3'-diisocyanate, 4,4'-di-tert-butyl-diphenylsulfone-3,3'-diisocyanate, 4,4'-methoxybenzene ethylenedisulfone-3,3'-diisocyanate and 4,4'-dichlorodiphenylsulfone-3,3'-diisocyanate;

sulfonic ester-type polyisocyanates such as 4-methyl-3-isocyanatobenzenesulfonyl-4'-isocyanato-phenol ester, 4-methoxy-3-isocyanatobenzenesulfonyl-4'-isocyanato-phenol ester;

aromatic sulfonic amides such as 4-methyl-3-isocyanatobenzene-sulfonylanilide-3'-methyl-4'-isocyanate, dibenzenesulfonyl-ethylenediamine-4,4'-diisocyanate, 4,4'-methoxybenzenesulfonyl-ethylenediamine-3,3'-diisocyanate and 4-methyl-3-isocyanatobenzene-sulfonylanilide-4-methyl-3'-isocyanate; and sulfur-containing heterocyclic compounds such as thiophene-2,5-diisocyanate, thiophene-2,5-diisocyanatomethyl and 1,4-dithian-2,5-diisocyanate.

Halogenated derivatives such as chlorinated and brominated derivatives, alkylated derivatives, alkoxylated derivatives, nitrated derivatives, prepolymer type addition products with polyhydric alcohols, carbodiimide modified derivatives, urea modified derivatives, biuret modified derivatives and dimerization or trimerization products of these polyisocyanate compounds may also be used in the present invention.

The polyisothiocyanate compound used as a raw material in the present invention has two or more —NCS groups in the molecule and may also contain sulfur atom or atoms in addition to the isothiocyanate groups.

The polyisothiocyanate compound includes, for example, aliphatic polyisothiocyanates such as 1,2-diisothiocyanatoethane, 1,3-diisothiocyanatopropane, 1,4-diisothiocyanatobutane, 1,6-diisothiocyanatohexane and p-phenylenediisopropylidene diisothiocyanate;

alicyclic polyisothiocyanates such as cyclohexane diisothiocyanate;

aromatic polyisothiocyanates such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-diisothiocyanato-1,1'-biphenyl, 1,1'-methylenebis(4-isothiocyanatobenzene), 1,1'-methylenebis(4-isothiocyanato-2-methylbenzene), 1,1'-methylenebis(4-isothiocyanato-3-methylbenzene), 1,1'-(1,2-ethanediyl)bis(4-isothiocyanatobenzene), 4,4'-diisothiocyanatobenzophenone, 4,4'-diiso-thiocyanato-3,3'-dimethylbenzophenone, benzanilide-3,4'-diisothiocyanate, diphenylether-4,4'-diisothiocyanate and diphenylamine-4,4'-diisothiocyanate;

heterocyclic polyisothiocyanates such as 2,4,6-triisothiocyanato-1,3,5-triazine; and carbonyl polyisothiocyanates such as hexane-dioyl diisothiocyanate, nonanedioyl diisothiocyanate, carbonic diisothiocyanate, 1,3-benzenedicarbonyl diisothiocyanate, 1,4-benzenedicarbonyl diisothiocyanate and (2,2'-bipyridine)-4,4'-dicarbonyl diisothiocyanate.

The polyisothiocyanate having one or more sulfur atoms in addition to the isothiocyanate groups and two or more functional groups used as a raw material in the present invention includes, for example, sulfur-containing aliphatic polyisothiocyanates such as thiobis(3-isothiocyanatopropane), thiobis(2-isothiocyanatoethane) and dithiobis(2-isothiocyanato-ethane);

sulfur-containing aromatic polyisothiocyanates such as 1-isothiocyanato-4-[(2-isothiocyanato)sulfonyl] benzene, thiobis(4-isothiocyanatobenzene), sulfonylbis(4-isothiocyanatobenzene), sulfinylbis(4-isothiocyanatobenzene), dithiobis(4-isothiocyanatobenzene), 4isothiocyanato-1-[(4-isothiocyanatophenyl)-sulfonyl]-2-methoxybenzene, 4-methyl-3-isothiocyanatobenzene-sulfony-4'-isothiocyanate phenyl ester and 4-methyl-3-isothiocyanatobenzene-sulfonylanilide-3'-methyl-4'-isothiocyanate; and sulfur-containing heterocyclic compounds such as thiophene-2,5-diisothiocyanate and 1,4-dithian-2,5-diisothiocyanate.

Further, halogenated derivatives such as chlorinated and brominated derivatives, alkylated derivatives, alkoxylated derivatives, nitrated derivatives, prepolymer type addition products with polyhydric alcohols, carbodiimide modified derivatives, urea modified derivatives, biuret modified derivatives and dimerization and trimerization products of these polyisothiocyanate compounds may also be used in the present invention.

The isocyanato-containing polyisothiocyanate compound used as a raw material in the present invention includes, for example, aliphatic and alicyclic compounds such as 1-isothiocyanato-3-isocyanatopropane, 1-isothiocyanato-5-isocyanatopentane, 1-isothiocyanato-6-isocyanatohexane, isothiocyanatocarbonyl isocyanate and 1-isothiocyanato-4-isocyanatocylohexane;

aromatic compounds such as 1-isothiocyanato-4-isocyanatobenzene and 4-methyl-3-isothiocyanato-1-isozcyanatobenzene;

heterocyclic compounds such as 2-isocyanato-4,5-diisothiocyanato-1,3,5-triazine; and compounds having sulfur atoms in addition to isothiocyanate groups such as 4-isocyanato-4'-isothiocyanatodiphenyl sulfide and 2-isocyanato-2'-isothiocyanatodiethyl disulfide.

Further, halogenated derivatives such as chlorinated and brominated derivatives, alkylated derivatives, alkoxylated derivatives, nitrated derivatives, prepolymer type addition products with polyhydric alcohols, carbodilmide modified derivatives, urea modified derivatives, biuret modified derivatives and dimerization or trimerization products of these compounds may also be used in the present invention.

These isocyanates may be used singly or as a mixture of two or more of them.

The active hydrogen compound used as a modifier of the sulfur-containing urethane-based resin of the present invention is selected from hydroxyl compounds, mercapto compounds and hydroxylated mercapto compounds.

The hydroxyl compounds include, for example, methanol, benzyl alcohol, phenol, ethoxy ethanol;

aliphatic polyols such as ethylene glycol, diethylene glycol, propylene glycol, dipropylene glycol, butylene glycol, neopentyl glycol, glycerol, trimethylolethane, trimethylolpropane, butanetriol, 1,2-methylglucoside, pentaerythritol, dipentaerythritol, tripentaerythritol, sorbitol, erythritol, threitol, ribitol, arabinitol, xylitol, allitol, mannitol, dulcitol, iditol, glycol, inositol, hexanetriol, triglycerol, diglycerol, triethylene glycol, polyethylene glycol, tris(2-hydroxyethyl)-isocyanurate, cyclo-butanediol, cyclopentanediol, cyclohexanediol, cycloheptanediol, cyclooctanediol, cyclohexanedimethanol, hydroxypropyl-cyclohexanol, tricyclo[5,2,1,0,2,6]-decanedimethanol, bicyclo[4,3,0] nonanediol, dicyclohexanediol, tricyclo[5.3.1.1] dodecanediol, bicyclo[4.3.0]-nonane-dimethanol, tricyclo[5.3.1.1]-dodecane-diethanol, hydroxypropyl-tricyclo[5.3.1.1]dodecanol, spiro[3.4]-octanediol, butylcyclohexanediol, 1,1'-bicyclohexylidenediol, cyclohexanetriol, maltitol and lactitol;

aromatic polyols such as dihyroxynaphthalene trihydroxynaphthalene, tetrahydroxynaphthalene, dihydroxybenzene, benzenetriol, biphenyltetraol, pyrogallol, (hydroxynaphthyl)-pyrogallol, trihydroxyphenanthrene, bisphenol-A, bisphenol-F, xylyleneglycol, di(2-hydroxyethoxy)benzene, bisphenol-A-bis(2-hydroxyethylether), tetrabromobisphenol-A and tetrabromobisphenol-A-bis(2-hydroxyethylether);

halogenated polyols such as dibromoneopentylglycol;

high molecular polyols such as epoxy resin;

condensed products of the above-mentioned polyols with organic acids such as oxalic acid, glutamic acid, adipic acid, acetic acid, propionic acid, cyclohexanecarboxylic acid, β-oxo-cyclohexanepropionic acid, dimer acid, phthalic acid, isophthalic acid, salicylic acid, 3-bromopropionic acid, 2-bromoglycolic acid, cyclohexanedicarboxylic acid, pyromellitic acid, butanetetracarboxylic acid and bromophthalic acid;

addition products of alkylene oxides such as ethylene oxide and propylene oxide to the above polyols and to alkylenepolyamines; and sulfur-containing polyols such as bis[4-(hydroxyethoxy) phenyl] sulfide, bis[4-(2-hydroxypropoxy)phenyl] sulfide, bis[4-(2,3-dihydroxypropoxy)phenyl] sulfide, bis[4-(4-hydroxycyclohexyloxy)-phenyl] sulfide, bis [2-methyl-4-(hydroxyethoxy)-6-butylphenyl] sulfide, compounds obtained by the addition of ethylene oxide and/or propylene oxide to the sulfur-containing polyols in an amount of not more than 3 moles on average per mole of hydroxyl group of the polyols, di(2-hydroxyethyl) sulfide, 1,2-bis(2-hydroxyethylmercapto)ethane, bis(2-hydroxyethyl) disulfide, 1,4-dithian-2,5-diol, bis(2,3-dihydroxypropyl) sulfide, tetrakis(4-hydroxy-2- thiabutyl)methane, bis(4-hydroxyphenyl) sulfone (trade name : Bisphenol-S), tetrabromobisphenol-S, tetramethylbisphenol-S, 4,4'-thiobis(6-tert-butyl-3-methylphenol) and 1,3-bis(2-hydroxyethylthioethyl) cyclohexane.

The mercapto compounds include, for example, methyl mercaptan, benzenethiol, benzylthiol; aliphatic polythiols such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, tetrakis(mercaptomethyl)-methane, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2.2.1]hepta-exo-cis-2,3-dithiol, 1,1-bis(mercaptomethyl) cyclohexane, thiomalic acid bis(2-mercaptoethyl ester), 2,3-dimercaptosuccinic acid (2-mercapto-ethyl ester), 2,3-dimercapto-1-propanol (2-mercaptoacetate), 2,3-dimercapto-1-propanol (3-mercaptoacetate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethylene glycol bis(2-mercapto-acetate), ethylene glycol bis(3-mercaptopropionate), trimethylol-propane tris(2-mercaptoacetate), trimethylolpropane tris(3-mercaptopropionate), pentaerythritol tetrakis(2-mercaptoacetate), pentaerythritol tetrakis(3-mercaptopropionate) and 1,2-bis(2-mercaptoethylthio)-3-mercaptopropane;

aromatic polythiols such as 1,2-dimercaptobenzene, 1,3-dimercaptobenzene, 1,4-dimercaptobenzene, 1,2-bis(mercaptomethyl)benzene, 1,3-bis(mercaptomethyl) benzene 1,4-bis(mercaptomethyl)benzene, 1,2-bis(mercaptoethyl)benzene, 1,3-bis(mercaptoethyl) benzene, 1,4-bis(mercaptoethly)benzene, 1,2-bis(mercaptomethyleneoxy)benzene, 1,3-bis(mercaptomethyleneoxy)benzene, 1,4-bis(mercaptomethyleneoxy)benzene, 1,2-bis(mercaptoethyleneoxy)benzene, 1,3-bis(mercaptoethyleneoxy)benzene, 1,4-bis(mercaptoethyleneoxy)benzene, 1,2,3-trimercaptobenzene, 1,2,4-trimercaptobenzene, 1,3,5-trimercaptobenzene, 1,2,3-tris(mercaptomethyl) benzene, 1,2,4-tris(mercaptomethyl) benzene, 1,3,5-tris(mercaptomethyl)benzene, 1,2,3-tris(mercaptoethyl)benzene, 1,2,4-tris(mercaptoethyl) benzene, 1,3,5-tris(mercaptoethyl)benzene, 1,2,3-tris(mercaptomethyleneoxy)benzene, 1,2,4-tris(mercaptomethyleneoxy)benzene, 1,3,5-tris(mercaptomethyleneoxy)benzene, 1,2,3-tris(mercaptoethyleneoxy)benzene, 1,2,4-tris(mercaptoethyleneoxy) benzene, 1,3,5-tris(mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 1,2,3,4-tetrakis(mercaptomethyleneoxy)benzene, 1,2,3,5-tetrakis(mercaptomethyleneoxy)benzene, 1,2,4,5-tetrakis(mercaptomethyleneoxy)benzene, 1,2,3,4-tetrkis(mercapto-ethyleneoxy)benzene, 1,2,3,5-tetrakis(mercaptoethyleneoxy)benzene, 1,2,4,5-tetrakis(mercaptoethyleneoxy)benzene, 2,2'-dimercaptobiphenyl, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracene-dimethanethiol, 1,3-di(p-methoxyphenyl)propane-2,2-dithiol, 1,3-diphenylpropane-2,2-dithiol, phenylmethane-1,1-dithiol and 2,4-di(p-mercaptophenyl)pentane;

halogenated aromatic polythiols including chlorinated or brominated polythiols such as 2,5-dichlorobenzene-1,3-dithiol, 1,3-di(p-chlorophenyl)propane-2,2-dithiol, 3,4,5-tribromo-1,2-dimercaptobenzene and 2,3,4,6-tetrachloro-1,5-bis(mercaptomethyl)benzene; heterocyclic polythiols such as 2-methylamino-4,6-dithiol-sym-triazine, 2-ethylamino-4,6-dithiol-sym-triazine, 2-amino-4,6-dithiol-sym-triazine, 2-morphorino-4,6-dithiol-sym-triazine, 2-cyclohexyl-amino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine and 2-thiobutyloxy-4,6-dithiol-sym-triazine;

aromatic polythiols containing sulfur atoms in addition to mercapto groups such as 1,2-bis(mercaptomethylthio) benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercapto-methylthio) benzene, 1,2,4,5-tetrakis(mercaptomethylthio)benzene, 1,2,3,4-tetrakis(mercaptoethylthio)benzene, 1,2,3,5-tetrakis(mercaptoethylthio)benzene, 1,2,4,5-tetrakis(mercaptoethylthio)benzene and aromatic ring alkylated derivatives of these polythiols;

aliphatic polythiols containing sulfur atoms in addition to mercapto groups such as bis(mercaptomethyl) sulfide, bis(mercaptoethyl) sulfide, bis(mercaptopropyl) sulfide, bis(mercaptomethylthio)methane, bis(2-mercaptoethylthio) methane, bis(3-mercaptopropylthio)methane, 1,2-bis(mercaptomethylthio) ethane, 1,2-bis(2-mercaptoethylthio)ethane, 1,2-bis(3-mercaptopropylthio)ethane, 1,3-bis(mercaptomethylthio)propane, 1,3-bis(2-mercaptoethylthio)propane, 1,3-bis(3-mercaptopropylthio)propane, 1,2-bis(2-mercaptoethylthio)-3-mercaptopropane, 2-mercaptoethylthio-1,3-propanedithiol, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrkis(2-mercaptoethylthiomethyl)methane, tetrakis(3-mercaptopropylthiomethyl) methane, bis(2,3-dimercaptopropyl) sulfide, 2,5-dimercapto-1,4-dithian, bis(mercaptomethyl) disulfide, bis(mercaptoethyl) disulfide and bis(mercaptopropyl) disulfide; esters of mercaptoacetic acid and mercaptopropionic acid with these compounds;

aliphatic polythiols containing sulfur atoms in addition to mercapto groups such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithian-2,5-diol bis(2-mercaptoacetate), 1,4-dithian-2,5-diol bis(3-mercaptopropionate), thioglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithiodiglycolic acid bis(2,3-dimercaptopropyl ester) and dithiodipropionic acid bis (2,3-dimercaptopropyl ester); and heterocyclic compounds containing sulfur atoms in addition to mercapto groups such as 3,4-thiophene-dithiol, 2,5-dimercapto-1,3,4-thiadiazol, 2,5-dimercapto-1,4-dithan and 2,5-dimercaptomethyl-1,4-dithian.

The hydroxylated mercapto compound includes, for example, 2-mercaptoethanol, 3-mercapto-1,2-propanediol, glycerol di(mercaptoacetate), 1-hydroxy-4-mercaptocyclohexane, 2,4-dimercaptophenol, 2-mercaptohydroquinone, 4-mercaptophenol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyltris(mercaptoethylthiomethyl)methane, 1-hydroxyethylthio-3-mercaptoethylthiobenzene, 4-hydroxy-4'-mercaptodiphenyl sulfone, 2-(2-mercaptoethylthio)ethanol, dihydroxyethyl sulfide mono(3-mercaptopropionate), dimercaptoethane monosalicylate and hydroxyethylthiomethyl-tris(nercaptoethylthio)methane.

Further, halogenated derivatives such as chlorinated and brominated derivatives of the active hydrogen compounds may also be used in the present invention. They may be used singly or as a mixture of two or more of them.

The monocyanate used as a modifier of the sulfurcontaining urethane-based resin of the present invention is selected from monoisocyanate compounds and monoisothiocyanate compounds.

The monoisocyanate compounds include, for example, phenyl isocyanate, butyl isocyanate, cyclohexyl isocyanate, etc.

The monoisothiocyanate compounds include, for example, phenyl isothiocyanate, butyl isothiocyanate, cyclohexyl isothiocyanate, etc.

Halogenated derivatives such as chlorinated or brominated derivatives, alkylated derivatives, alkoxylated derivatives and nitrated derivatives of these compounds may also be used. They may be used singly or as a mixture of two or more of them.

The proportion of at least one isocyanate selected from the polyisocyanate compounds, polyisothiocyanate compounds and isocyanato-containing polyisothiocyanate compounds to the polythiol is generally 0.5 to 3.0, preferably 0.5 to 1.5 in terms of the molar ratio of the functional groups (NCO+NCS)/SH.

The plastic lens of the present invention is made of an S-alkyl thiocarbamate resin or a dithiourethane resin. The resins are primarily composed respectively of S-alkyl thiocarbamate bonds formed by reacting isocyanate groups with mercapto groups and dithiourethane bonds formed by reacting isothiocyanate groups with mercapto groups. The resins may also contain allophanate bonds, urea bonds, thiourea bonds, biuret bonds, etc. in addition to the above described bonds for desired purposes.

For example, when S-alkyl thiocarbamate bonds are additionally reacted with isocyanate groups or dithiourethane bonds are further reacted with isothiocyanate groups to increase crosslinking density, favorable results are often obtained. In such reactions, the temperature should be raised to at least 100° C. and the amount of the isocyanate or isothiocyanate component should be increased. Further, an amine or the like may be used partially in combination to form urea bonds or biuret bonds. However, particular attention should be paid to the coloring of the resin and/or lens when a compound other than the active hydrogen compound is reacted with the isocyanate compound or isothiocyanate compound in the above manner.

A variety of agents such as an internal mold releasing agent, chain extender, crosslinking agent, light stabilizer, ultraviolet absorber, antioxidant, oil soluble dye and filler may be added to the resin in accordance with purposes in the same manner as in the molding processes known in the art.

To control the reaction rate at a desired value, it is also possible to add properly known reaction catalysts used in the production of polyurethane.

The lens of the present invention is generally prepared by a casting polymerization process. Specifically, a polyisocyanate is mixed with a polythiol having 4 or more functional groups represented by formulae (1) to (3). The mixture is deaerated by a suitable means, if necessary, and then poured into a mold where it is polymerized generally by increasing the temperature slowly from a low temperature of about 0 to 5° C. to a high temperature of about 100 to 180° C. Here, a known mold releasing treatment may be applied to the mold in advance to facilitate mold releasing after the polymerization.

The thus-obtained sulfur-containing urethane-based resin according to the present invention is of extremely low dispersion of refractive index, has a high refractive index, is excellent in heat resistance and colorless and transparent, has no optical distortion, is lightweight and has excellent characteristics in weatherability, dye-affinity, impact resistance, machinability, etc. so that it is suitably used as materials for optical elements such as eyeglass lenses and camera lenses and as materials for glazing materials, coating materials and adhesives.

The lens made of the sulfur-containing urethane-based resin according to the present invention may undergo physical and/or chemical treatments such as surface polishing, antistatic treatment, hard coat treatment, anti-reflection coat treatment, coloring treatment and dimming treatment in order to improve or impart such properties as anti-reflection, high hardness, abrasion resistance, chemical resistance, fog resistance and fashion-ability, as required.

The present invention will be described in more detail by reference to the following Examples and Comparative Examples. In the performance tests of the lenses obtained, refractive index, Abbe's number, weatherability, optical distortion, impact resistance, heat resistance and dye-affinity are evaluated in accordance with the following testing methods.

Refractive index and Abbe's number: Measured at 20° C. by means of a Pulfrich refractometer.

Weatherability: A sample of the resin was laid on a Weatherometer equipped with a sunshine carbon arc lamp. After a lapse of 200 hours, the resin was taken out and its hue was compared with the hue of the resin prior to the test. The criterion of evaluation was as follows: no change - - - (O); slightly yellowing - - - (Δ); and yellowing - - - (X).

Optical distortion: Determined visually means of a strain inspector: no optical distortion observed - - - (O); and optical distortion observed - - - (X).

Impact resistance: Measured in accordance with FDA a standard by dropping an iron ball of 16.3 g from a height of 127 cm: not broken - - - (O); cracked - - - (Δ); and broken - - - (X).

Heat resistance: Measured by the TMA method: resistant above 100° C. - - - (O); resistant at 90–100° C. - - - (Δ); and resistant below 90° C. - - - (X).

Dye-affinity: A resin specimen was immersed in a water dispersion containing 0.5% by weight of a disperse dye (MLP Blue-2 manufactured by Mitsui Toatsu Dye Ltd.) under stirring. After 10 minutes, the specimen was taken out and washed: dyed - - - (O); and not dyed - - - (X).

EXAMPLE 1

To a mixed solution of 78.1 g (1.0 mole) of 2-mercaptoethanol and 2.0 g of triethylamine were added 92.5 g (1.0 mole) of epichlorohydrin dropwise over an hour while maintaining the temperature at 35–45° C., followed by maturing at 40° C. for an hour.

An aqueous solution, formed in advance by dissolving 125.0 g (0.5 mole) of $Na_2S \cdot 9H_2O$ in 100 g of pure water, was added dropwise to the reaction liquid over an hour while maintaining the temperature at 40–45° C., followed by maturing at 45° C. for an hour, thereby obtaining the following tetrafunctional compound corresponding to formula (4). Identification was made by means of NMR.

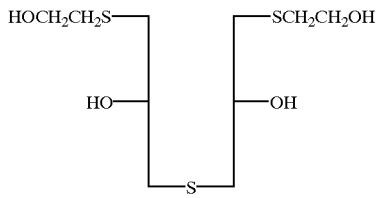

Then, 303.8 g (3.0 moles) of 36% hydrochloric acid and 190.3 g (2.5 moles) of thiourea were added to the reaction liquid and the mixture was heated at 110° C. for 9 hours under stirring.

The mixture was cooled to room temperature, to which were added 400 ml of toluene and then slowly 306.5 g (4.5 moles) of 25% aqueous ammonia, followed by hydrolysis at 60° C. for 3 hours.

The organic layer thus obtained was washed in sequence with 100 ml of 36% hydrochloric acid, 100 ml of water, 100 ml of dilute aqueous ammonia, and 100 ml of water twice.

The toluene was distilled off by a rotary evaporator and dust was separated by suction filtration to obtain 174.6 g (0.476 mole; yield 95.2%) of the below-described polythiol FSH4 as a colorless and transparent liquid.

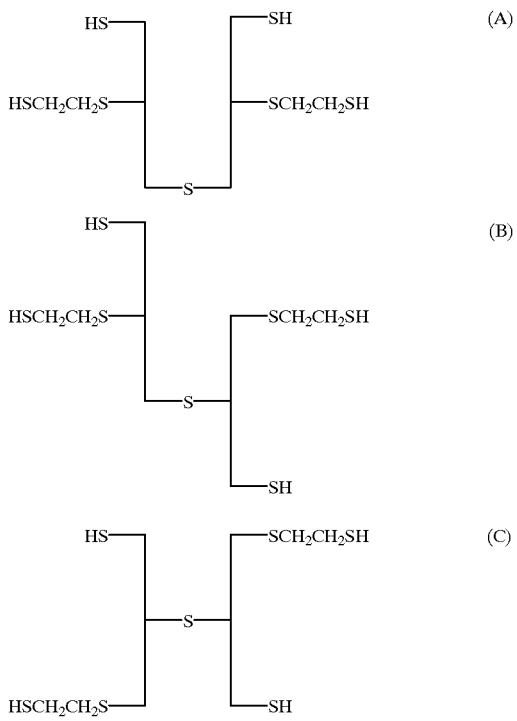

(A)/(B)/(C) = 85/5/10 (by mole)

These isomers were each isolated by reversed-phase chromatography to subject them to identification.

The results of elemental analysis, IR, MS and NMR of FSH4-(A) component

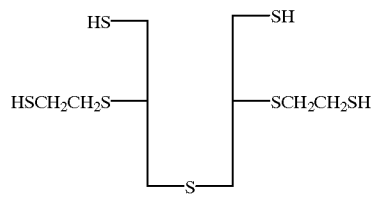

are shown below.

| <Elemental analysis> | | |
|---|---|---|
| | Found (%) | Calculated (%) |
| C | 32.7 | 32.8 |
| H | 6.2 | 6.1 |
| S | 61.1 | 61.2 |

<IR $\nu_{max}$ (KBr) $cm^{-1}$>
2543 (SH)
<MS>
m/z = 366 ($M^+$)
<$^{13}$C-NMR $CDCl_3$>

δ ppm

-continued

<Elemental analysis>

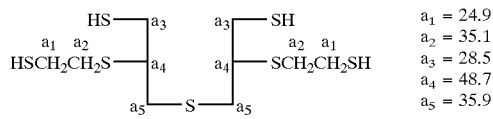

$a_1 = 24.9$
$a_2 = 35.1$
$a_3 = 28.5$
$a_4 = 48.7$
$a_5 = 35.9$

Then, the results for FSH4-(C) component

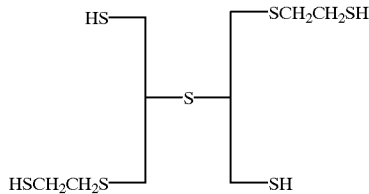

is shown below.

The results of elemental analysis, IR and MS were the same as those for the component (A).

<$^{13}$C-NMR CDCl$_3$>

δ ppm

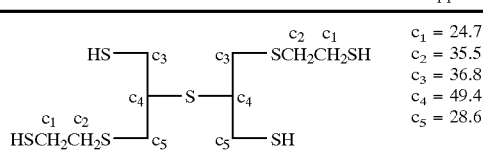

$c_1 = 24.7$
$c_2 = 35.5$
$c_3 = 36.8$
$c_4 = 49.4$
$c_5 = 28.6$

Finally, the results for FSH4-(B) component

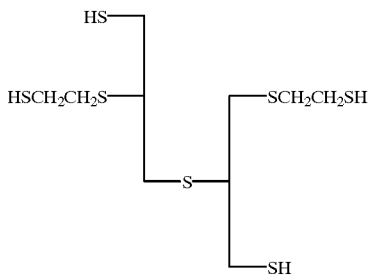

is shown below.

The results of elemental analysis, IR and MS were the same as those for the component (A).

<$^{13}$C-NMR CDCl$_3$>

δ ppm

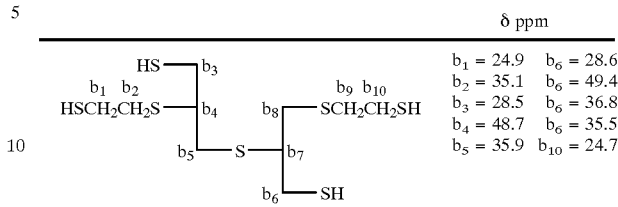

$b_1 = 24.9$  $b_6 = 28.6$
$b_2 = 35.1$  $b_6 = 49.4$
$b_3 = 28.5$  $b_6 = 36.8$
$b_4 = 48.7$  $b_6 = 35.5$
$b_5 = 35.9$  $b_{10} = 24.7$

EXAMPLE 2

To a mixed solution of 108.2 g (1.0 mole) of thioglycerol and 4.0 g of triethylamine were added 92.5 g (1.0 mole) of epichlorohydrin dropwise over an hour while maintaining the temperature at 45–50° C., followed by maturing at 50° C. for 0.5 hour, thereby obtaining the below-described tetrafunctional compound corresponding to formula (4). Identification was made similarly to Example 1 by means of NMR.

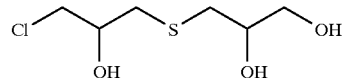

Then, 400.0 g (3.36 moles) of thionyl chloride were added dropwise to the reaction liquid over an hour at a temperature of 50° C., followed by maturing at 60° C. for 7 hours. The resulting liquid was cooled to room temperature, to which 100 g of pure water were added dropwise to decompose excess thionyl chloride. EDC in an amount of 300 g was added thereto to extract the chlorinated product.

The EDC layer was washed twice with 100 g of pure water and the EDC was distilled off under vacuum by a rotary evaporator to obtain 247.8 g (0.968 mole) of the following chlorinated derivatives corresponding to formula (4). Identification was made similarly by means of NMR.

 (E)

 (F)

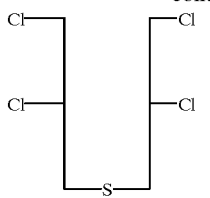

(E)/(F)/(G) = 5/20/75 (by mole)

Then, 368.4 g (4.84 moles) of thiourea and 500 g of pure water were added to the chlorinated derivatives, and the mixture was heated at 105° C. for an hour under stirring. The mixture was cooled to room temperature, to which were added 1.5 l of toluene and then slowly 500.0 g (8.92 moles) of hydrazine hydrate to hydrolyze the reaction product at 80° C. for an hour.

The organic layer thus obtained was subjected to purification and removal in the same manner as in Example 1 to obtain 225.9 g (0.917 mole; yield 91.7%) of the following polythiol FSH1 as a colorless, transparent and viscous liquid.

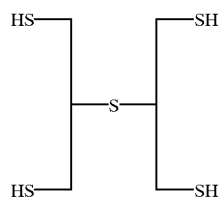

The results of elemental analysis, IR, MS and NMR are shown below.

| <Elemental analysis> | | |
|---|---|---|
| | Found (%) | Calculated (%) |
| C | 30.7 | 29.2 |
| H | 5.8 | 5.7 |
| S | 64.5 | 65.0 |

<IR $\nu_{max}$ (KBr) cm$^{-1}$>
2544 (SH)
<MS>
m/z = 246(M$^+$)
<$^{13}$C-NMR CDCl$_3$>

| | δ ppm |
|---|---|
| 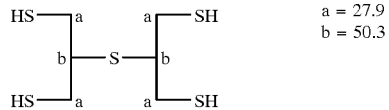 | a = 27.9 |
| | b = 50.3 |

EXAMPLE 3

To a liquid mixture of 78.1 g of 2-mercaptoethanol and 1.0 g of triethylamine were added 43.0 g (0.5 mole) of 1,2,3,4-butadienediepoxide dropwise over an hour at a temperature of 35–40° C., followed by maturing at 40° C. for an hour to obtain a colorless, transparent and viscous liquid. The liquid was identified as the following tetrafunctional compound corresponding to formula (6) from the data of NMR.

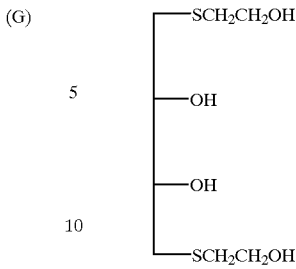

Then, 303.9 g (3.0 moles) of 36% hydrochloric acid and 190.3 g (2.5 moles) of thiourea were added to the reaction liquid, and the mixture was heated at 110° C. for 3 hours under stirring to carry out the reaction. The reaction mixture was cooled to room temperature, to which were added 300 ml of toluene and then slowly 272.4 g (4.0 moles) of 25% aqueous ammonia, followed by hydrolysis at 55–65° C. for 3 hours.

The organic layer was separated and then subjected to purification and removal in the same manner as in Example 1 to obtain 145.6 g (0.475 mole; yield 95.0%) of the following polythiol FSH2 as a colorless, transparent and viscous liquid.

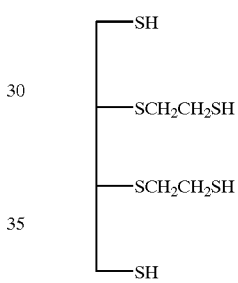

The results of elemental analysis, IR, MS and NMR are shown below.

| <Elemental analysis> | | |
|---|---|---|
| | Found (%) | Calculated (%) |
| C | 31.3 | 31.3 |
| H | 5.9 | 5.9 |
| S | 62.6 | 62.7 |

<IR $\nu_{max}$ (KBr) cm$^{-1}$>
2544 (SH)
<MS>
m/z = 306(M$^+$)
<$^{13}$C-NMR CDCl$_3$>

| | δ ppm |
|---|---|
| 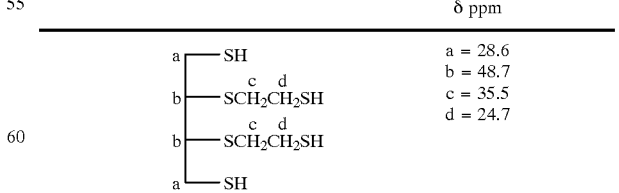 | a = 28.6 |
| | b = 48.7 |
| | c = 35.5 |
| | d = 24.7 |

EXAMPLE 4

To a liquid mixture of 78.1 g (1.0 mole) of 2-mercaptoethanol, 186.9 g (0.5 mole) of 1,2,3,4- tetrabromobutane and 500 ml of ethanol were added 81.6 g (1.0 mole) of 49% NaOH dropwise over 2 hours at a temperature of 40–60° C., followed by maturing at 50° C. for 2 hours. After completion of the reaction, the reaction mixture was cooled to room temperature and the NaBr thereby deposited was separated by filtration. The ethanol and water were distilled off the filtrate by an evaporator to obtain a colorless and viscous liquid. The liquid was identified as the following tetrafunctional compound corresponding to formula (6) from the data of NMR.

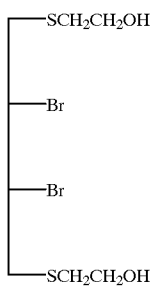

Then, 257.9 g (1.5 moles) of 47' hydrobromic acid and 190.3 g (2.5 moles) of thiourea were added to the viscous liquid. The mixture was subjected to isothiouronium salt reaction, hydrolysis, purification and removal in the same manner as in Example 3 to obtain 131.7 g (0.429 mole; yield 85.8%) of the following polythiol FSH2, the same polythiol as obtained in Example 3, as a colorless, transparent and viscous liquid.

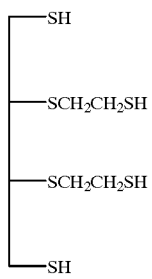

EXAMPLE 5

To a liquid mixture of 156.2 g (2.0 moles) of 2-mercaptoethanol, 186.9 g (0.5 mole) of 1,2,3,4-tetrabromobutane and 500 ml of DMF were added 163.2 g (2.0 moles) of 49% NaOH dropwise over 2 hours at a temperature of 40–60° C., followed by maturing at 100° C. for 5 hours. After completion of the reaction, the reaction mixture was cooled to room temperature and the NaBr thereby deposited was separated by filtration. The DMF and water were distilled off the filtrate by an evaporator to obtain a colorless and viscous liquid. The liquid was identified as the following tetrafunctional compound corresponding to formula (6) from the data of NMR.

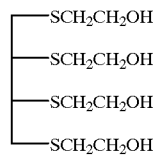

Then, 253.2 g (2.5 moles) of 36% hydrochloric acid and 152.2 g (2.0 moles) of thiourea were added to the viscous liquid. The mixture was subjected to isothiouronium salt reaction, hydrolysis, purification and removal in the same manner as in Example 3 to obtain 205.0 g (0.480 mole; yield 96.0%) of the following polythiol FSH5, as a colorless, transparent and viscous liquid.

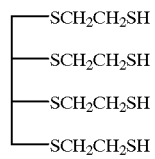

The results of elemental analysis, IR, MS and NMR are shown below.

| | <Elemental analysis> | |
|---|---|---|
| | Found (%) | Calculated (%) |
| C | 33.6 | 33.8 |
| H | 6.0 | 6.1 |
| S | 60.3 | 60.1 |

<IR ν$_{max}$ (KBr) cm$^{-1}$>
2544 (SH)
<MS>
m/z = 426(M$^+$)
<$^{13}$C-NMR CDCl$_3$>

| | δ ppm |
|---|---|
| a ┌─ SCH$_2$CH$_2$SH (e f) <br> b ├─ SCH$_2$CH$_2$SH (c d) <br> b ├─ SCH$_2$CH$_2$SH (c d) <br> a └─ SCH$_2$CH$_2$SH (e f) | a = 26.9 <br> b = 48.8 <br> c = 35.1 <br> d = 24.9 <br> e = 24.7 <br> f = 35.5 |

EXAMPLE 6

To a KOH solution, formed by dissolving 26.5 g (0.40 mole) of 85% KOH flake in 200 ml of isopropyl alcohol, were added dropwise 31.6 g (0.40 mole) of 2-mercaptoethanol at room temperature to carry out salt-forming.

Then, a solution, formed in advance by dissolving 52.4 g (0.20 mole) of pentaerythritol-dibromide-[2,2-bis (bromomethyl)-1,3-propanediol] in 170 ml of isopropyl alcohol, was added dropwise to the salt mass over an hour at a temperature of 70° C., followed by maturing at 70° C. for 3 hours. After completion of the reaction, the reaction mixture was cooled to room temperature, and the NaBr thereby deposited was separated by filtration. The isopropyl alcohol and water were distilled off the filtrate by an evaporator to obtain a colorless and viscous liquid. The liquid was identified as the following tetrafunctional compound corresponding to formula (5) from the data of NMR.

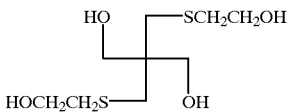

After 108.3 g (0.40 mole) of PBr$_3$ had been added dropwise to the viscous liquid at 50° C., the reaction was continued at 100° C. for 10 hours. After completion of the reaction, the reaction mixture was cooled to room temperature, to which were added 50 ml of pure water dropwise and then 200 ml of toluene to extract an organic layer.

The organic layer thus obtained was washed with 100 ml of an aqueous 1% NaHCO$_3$ solution once and then with 100 ml of pure water twice. The toluene was distilled off the organic layer by a rotary evaporator.

The remaining residue was identified as the following tetrafunctional compound corresponding to formula (5).

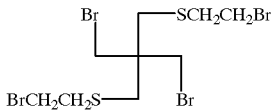

Subsequently, 112.2 g (2.00 moles) of NaSH were dissolved in 700 ml of DMF, to which 163.2 g (2.00 moles) of 49% NaOH were added slowly. After cooling the mixture to 30° C., 152.2 g (2.00 moles) of CS$_2$ were added thereto dropwise to carry out maturing at 40° C. for 2 hours. Thereafter, the foregoing brominated derivative dissolved in 200 ml of DMF was added slowly to the matured mixture to carry out the reaction at 100° C. for 2 hours.

The reaction liquid was cooled to room temperature, to which 300.0 g (2.96 moles) of 36% hydrochloric acid were added to hydrolyze the reaction product at 30° C. for an hour. The resultant reaction liquid was heated to 55° C. to recover the CS$_2$, and then cooled to room temperature. Subsequently, 800 ml of chloroform and 2,000 ml of water were added thereto to extract the product and the organic layer was separated. The organic layer was neutralized with 1% aqueous ammonia and washed with 500 ml of pure water three times. The chloroform was then removed by vacuum distillation.

The residue was added to a liquid mixture of 500 ml of toluene and 2,000 ml of ethanol, to which 10 g of zinc powder were added. To the resultant mixture were added 120 g (1.19 moles) of 36% hydrochloric acid dropwise while maintaining the temperature at 30° C. and then 500 g of pure water to extract the organic layer. The organic layer was washed with 300 ml of pure water three times, and the toluene was distilled off under vacuum to obtain 57.0 g (0.178 moles; yield 89.0%) of the following polythiol FSH3.

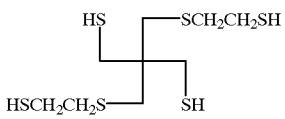

The results of elemental analysis, IR, MS and NMR are shown below.

| <Elemental analysis> | | |
|---|---|---|
| | Found (%) | Calculated (%) |
| C | 33.7 | 33.7 |
| H | 6.3 | 6.3 |
| S | 59.9 | 60.0 |

<IR ν$_{max}$ (KBr) cm$^{-1}$>
2544 (SH)
<MS>
m/z = 320(M$^+$)
<$^{13}$C-NMR CDCl$_3$>

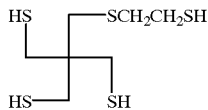

δ ppm a = 24.9
b = 35.1
c = 36.9
d = 14.6
e = 28.4

EXAMPLE 7

The following polythiol FSH6 was obtained in the same manner as in Example 6, except that the amounts of KOH flake and 2-mercaptoethanol were reduced to half of those used in Example 6.

HS⎯⎯SCH$_2$CH$_2$SH
HS⎯⎯SH

The results of elemental anaylsis, IR, MS and NMR are shown below.

| <Elemental analysis> | | |
|---|---|---|
| | Found (%) | Calculated (%) |
| C | 32.5 | 32.3 |
| H | 6.3 | 6.2 |
| S | 61.1 | 61.5 |

<IR ν$_{max}$ (KBr) cm$^{-1}$>
2544 (SH)
<MS>
m/z = 260(M$^+$)
<$^{13}$C-NMR CDCl$_3$>

δ ppm a = 24.9
b = 35.1
c = 36.9
d = 47.6
e = 28.4

EXAMPLE 8

Salt-forming was carried out in the same manner as in Example 6 by adding 71.1 g (0.60 mole) of 2-mercaptoethanol to a KOH solution formed by dissolving 39.8 g (0.60 mole) of 85% KOH flake in 300 ml of isopropyl alcohol. The salt mass thus formed was reacted with 77.5 g (0.20 mole) of pentaerythritol tetrabromide in the same manner as in Example 6 to obtain the following tetrafunctional compound. Identification was made by means of NMR.

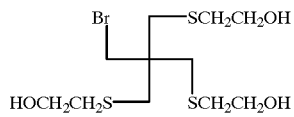

The compound was thiolated by the use of the isothiouronium salt process in the same manner as in Example 1 to obtain the following polythiol FSH7.

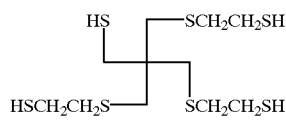

The results of elemental analysis, IR, MS and NMR are shown below.

| <Elemental analysis> | | |
|---|---|---|
| | Found (%) | Calculated (%) |
| C | 34.7 | 34.7 |
| H | 6.3 | 6.4 |
| S | 58.8 | 58.9 |

<IR ν$_{max}$ (KBr) cm$^{-1}$>
2544 (SH)
<MS>
m/z = 380(M$^+$)
<$^{13}$C-NMR CDCl$_3$>

| δ ppm |
|---|
| a = 24.9 |
| b = 35.1 |
| c = 36.9 |
| d = 47.6 |
| e = 28.4 |

EXAMPLE 9

The following compound was obtained in the same manner as in Example 3 except that the amount of 2-mercaptoethanol was reduced to half. Identification was made by means of NMR.

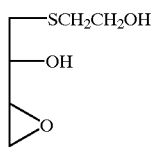

The following polythiol FSH8 was obtained by bromination and thiolation in the same manner as in Example 6.

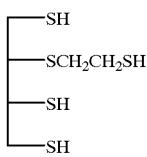

The results of elemental analysis, IR, MS and NMR are shown below.

| <Elemental analysis> | | |
|---|---|---|
| | Found (%) | Calculated (%) |
| C | 29.2 | 29.2 |
| H | 5.7 | 5.7 |
| S | 65.0 | 65.0 |

<IR ν$_{max}$ (KBr) cm$^{-1}$>
2544 (SH)
<MS>
m/z = 246(M$^+$)
<$^{13}$C-NMR CDCl$_3$>

| δ ppm |
|---|
| a = 24.9 |
| b = 35.1 |
| c = 28.5 |
| d = 48.7 |
| e = 40.4 |
| f = 28.4 |

EXAMPLE 10

To a liquid mixture of 39.1 g (0.50 mole) of 2-mercaptoethanol and 1.0 g of triethylamine were added dropwise 46.3 g (0.50 mole) of epichlorohydrin at a temperature of 35–40° C., followed by maturing at 40° C. for an hour.

After introducing 54.1 g (0.50 mole) of 1-thioglycerol into the reaction liquid, 40.8 g (0.50 mole) of 49% NaOH were added thereto dropwise at a temperature of 35–40° C., and the resultant reaction liquid was matured at 40° C. for an hour to obtain the following tetrafuctional compound. Identification was made by means of NMR.

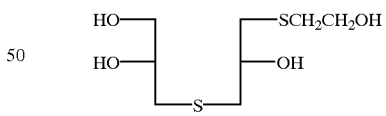

Then, the compound was brominated in the same manner as in Example 6 and thiolated in the same manner as in Example 2, thereby obtaining the following polythiol FSH9.

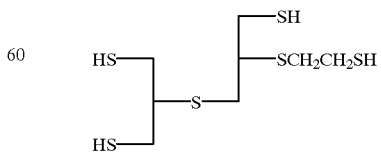

The results of elemental analysis, IR, MS and NMR are shown below.

| <Elemental analysis> | | |
|---|---|---|
| | Found (%) | Calculated (%) |
| C | 31.2 | 31.1 |
| H | 5.9 | 5.9 |
| S | 62.8 | 63.0 |

<IR ν$_{max}$ (KBr) cm$^{-1}$>
2544 (SH)
<MS>
m/z = 306(M$^+$)
<$^{13}$C-NMR CDCl$_3$>

| | δ ppm |
|---|---|
| (structure with labels a–g) | a = 27.9<br>b = 50.3<br>c = 35.9<br>d = 48.7<br>e = 28.5<br>f = 35.1<br>g = 24.9 |

EXAMPLE 11

To a liquid mixture comprising 128.0 g (0.50 mole) of the following chlorinated derivatives obtained in Example 2:

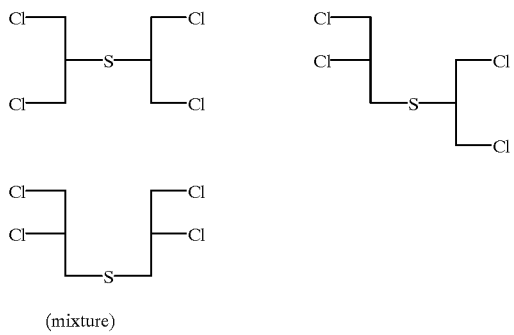

(mixture)

and 156.2 g (2.00 moles) of 2-mercaptoethanol were added dropwise 163.3 g (2.00 moles) of 49% NaOH at 35–40° C., followed by maturing at 50° C. for 2 hours, thereby obtaining the following polyols. Identification was made by means of NMR.

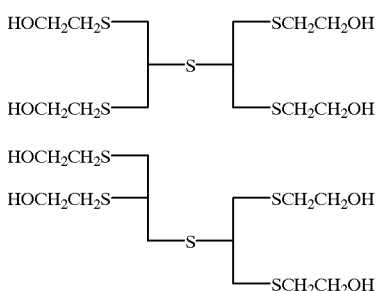

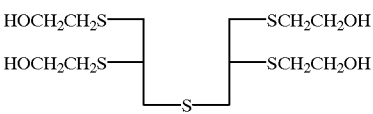

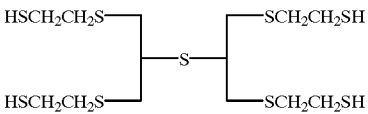

-continued (mixture)

These polyols were thiolated in the same manner as in Example 1 to obtain the following polythiol FSH10.

The results of elemental analysis, IR, MS and NMR are shown below.

| <Elemental analysis> | | |
|---|---|---|
| | Found (%) | Calculated (%) |
| C | 34.2 | 34.3 |
| H | 6.2 | 6.2 |
| S | 59.2 | 59.3 |

<IR ν$_{max}$ (KBr) cm$^{-1}$>
2544 (SH)
<MS>
m/z = 486 (M$^+$)
<$^{13}$C-NMR CDCl$_3$>

| | δ ppm |
|---|---|
| (structure with labels a–d) | a = 24.7<br>b = 35.5<br>c = 36.8<br>d = 49.4 |

EXAMPLE 12

In the same manner as in Example 3, 39.1 g (0.50 mole) of 2-mercaptoethanol were reacted with 43.0 g (0.50 mole) of 1,2,3,4-butadienediepoxide. The reaction product was further reacted with 54.1 g (0.50 mole) of 1-thioglycerol to obtain the following polyol.

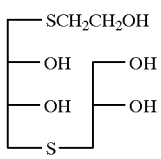

The polyol was chlorinated, polythiolated and purified by the procedure of Example 2 to obtain the following polythiol FSH11.

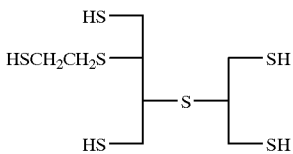

The results of elemental analysis, IR, MS and NMR are shown below.

| <Elemental analysis> | | |
|---|---|---|
| | Found (%) | Calculated (%) |
| C | 30.6 | 30.6 |
| H | 5.7 | 5.7 |
| S | 63.4 | 63.6 |

<IR $\nu_{max}$ (KBr) cm$^{-1}$>
2544 (SH)
<MS>
m/z = 352 (M$^+$)
<$^{13}$C-NMR CDCl$_3$>

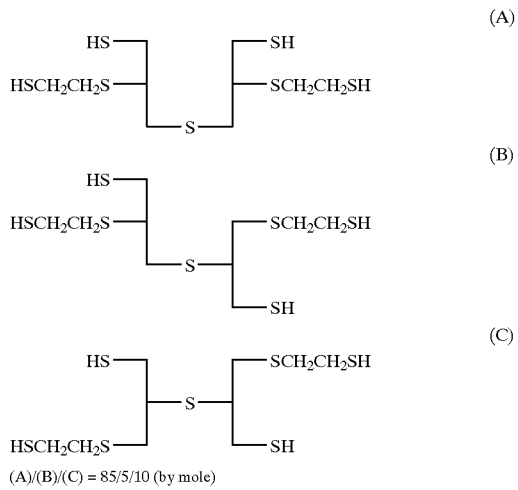

a = 24.9
b = 35.5
c = 28.6
d = 24.7
e = 49.5
f = 28.7
g = 50.4
h = 28.0

EXAMPLE 13

The following isomer mixture polythiol FSH4 synthesized in Example 1 in an amount of 36.7 g (0.10 mole) was mixed uniformly with 37.6 g (0.20 mole) of m-xylylenediisocyanate (hereinafter referred to as XDi). The mixture was charged into a mold consisting of a glass mold and a gasket made of a thermoplastic elastomer manufactured by Mitsui Petrochemical Industries, Ltd., where the mixture was cured by heating at 20–120° C. for 12 hours.

The sulfur-containing urethane-based plastic lens thus obtained was colorless and transparent and had entirely no cloudiness at the periphery due to the bleeding from the gasket. The properties of the lens are illustrated in Table 1. The IR chart of the resin obtained is shown in FIG. 1.

COMPARATIVE EXAMPLE 1

A sulfur-containing urethane-based lens was obtained by resinifying 41.7 g (0.16 mole) of GST (1,2-bis (mercaptoethylthio)-3-propanethiol) and 45.2 g (0.24 mole) of XDi under conditions of Example 13.

The center part of the lens was colorless and transparent and had no problems, but cloudiness was observed at the periphery due to the bleeding from the gasket.

The properties of the lens thus obtained are given in Table 2.

COMPARATIVE EXAMPLE 2

A sulfur-containing urethane-based lens was obtained by forming a resin from 32.1 g (0.16 mole) of GMT (1,2-bis (mercaptoethylthio)-1,3-propanedithiol) and 45.2 g (0.24 mole) of XDi under conditions of Example 13.

As a result, cloudiness was observed at the periphery due to the bleeding from the gasket, similarly to Comparative Example 1. The properties of the lens thus obtained are given in Table 2.

COMPARATIVE EXAMPLE 3

A sulfur-containing urethane-based lens was obtained by forming a resin from 34.6 g (0.17 mole) of PET (tetrakis (mercaptomethyl)methane) and 65.4 g (0.34 mole) of XDi under conditions of Example 13.

The lens had no cloudiness at the periphery due to the bleeding from the gasket and was colorless and transparent as a whole. However, it could hardly be dyed.

The properties of the lens thus obtained are given in Table 2.

COMPARATIVE EXAMPLE 4

A sulfur-containing urethane-based lens was obtained by forming a resin from 30.5 g (0.15 mole) of PET, 122.4 g (0.47 mole) of GST and 188.2 g (1.00 mole) of XDi under conditions of Example 13.

As a result, cloudiness was observed at the periphery due to the bleeding from the gasket, similarly to Comparative Example 1. The properties of the lens thus obtained are given in Table 2.

EXAMPLES 14–47 AND COMPARATIVE EXAMPLES 5–10

Sulfur-containing urethane-based plastic lenses were produced in the same manner as in Example 13. The results are shown in Tables 1 and 2. All the lenses obtained in the Examples were colorless and transparent and had entirely no cloudiness at the periphery due to bleeding from the gasket.

TABLE 1

| Example | Novel Polythiol (mol) | Isocyanate (mol) | Modifier (mol) | Refractive index | Abbe's number | Specific gravity | Heat resistance | Dye affinity | Impact resistance | Weatherability | Optical distortion |
|---|---|---|---|---|---|---|---|---|---|---|---|
| 13 | FSH4 mixture (0.10) | XDi (0.20) | | 1.66 | 32 | 1.37 | ○ | ○ | ○ | ○ | ○ |
| 14 | FSH4 (A) (0.10) | XDi (0.20) | | 1.66 | 32 | 1.37 | ○ | ○ | ○ | ○ | ○ |
| 15 | FSH4 (B) (0.10) | XDi (0.20) | | 1.66 | 32 | 1.37 | ○ | ○ | ○ | ○ | ○ |
| 16 | FSH4 (C) (0.10) | XDi (0.20) | | 1.66 | 32 | 1.37 | ○ | ○ | ○ | ○ | ○ |
| 17 | FSH1 (0.07) | XDi (0.20) | GST (0.04) | 1.66 | 32 | 1.36 | ○ | ○ | ○ | ○ | ○ |
| 18 | FSH2 (0.10) | XDi (0.20) | | 1.66 | 32 | 1.36 | ○ | ○ | ○ | ○ | ○ |
| 19 | FSH3 (0.10) | XDi (0.20) | | 1.66 | 32 | 1.36 | ○ | ○ | ○ | ○ | ○ |
| 20 | FSH6 (0.07) | XDi (0.20) | GST (0.04) | 1.66 | 32 | 1.36 | ○ | ○ | ○ | ○ | ○ |
| 21 | FSH8 (0.07) | XDi (0.20) | GST (0.04) | 1.66 | 32 | 1.35 | ○ | ○ | ○ | ○ | ○ |
| 22 | FSH9 (0.078) | XDi (0.20) | GST (0.03) | 1.66 | 32 | 1.36 | ○ | ○ | ○ | ○ | ○ |
| 23 | FSH11 (0.07) | XDi (0.20) | GST (0.04) | 1.66 | 32 | 1.35 | ○ | ○ | ○ | ○ | ○ |
| 24 | FSH1 (0.10) | BIMD (0.20) | | 1.70 | 31 | 1.54 | ○ | ○ | ○ | ○ | ○ |
| 25 | FSH2 (0.10) | BIMD (0.20) | | 1.70 | 31 | 1.53 | ○ | ○ | ○ | ○ | ○ |
| 26 | FSH6 (0.10) | BIMD (0.20) | | 1.70 | 31 | 1.54 | ○ | ○ | ○ | ○ | ○ |
| 27 | FSH8 (0.10) | BIMD (0.20) | | 1.70 | 31 | 1.53 | ○ | ○ | ○ | ○ | ○ |
| 28 | FSH9 (0.10) | BIMD (0.20) | | 1.70 | 31 | 1.54 | ○ | ○ | ○ | ○ | ○ |
| 29 | FSH11 (0.10) | BIMD (0.20) | | 1.70 | 31 | 1.53 | ○ | ○ | ○ | ○ | ○ |
| 30 | FSH1 (0.10) | XDi (0.20) | | 1.60 | 40 | 1.28 | ○ | ○ | ○ | ○ | ○ |
| 31 | FSH2 (0.10) | HMDi (0.10) TMDi (0.10) | | 1.60 | 41 | 1.22 | ○ | ○ | ○ | ○ | ○ |
| 32 | FSH3 (0.10) | HMDi (0.10) TMDi (0.10) | | 1.60 | 41 | 1.23 | ○ | ○ | ○ | ○ | ○ |
| 33 | FSH4 (0.10) | HMDi (0.10) TMDi (0.10) | | 1.60 | 41 | 1.25 | ○ | ○ | ○ | ○ | ○ |
| 34 | FSH5 (0.10) | HMDi (0.20) | | 1.60 | 42 | 1.24 | ○ | ○ | ○ | ○ | ○ |
| 35 | FSH7 (0.10) | HMDi (0.10) TMDi (0.10) | | 1.60 | 42 | 1.24 | ○ | ○ | ○ | ○ | ○ |
| 36 | FSH10 (0.10) | HMDi (0.20) | | 1.60 | 42 | 1.24 | ○ | ○ | ○ | ○ | ○ |
| 37 | FSH4 (0.10) | H6XDi (0.20) | | 1.60 | 41 | 1.30 | ○ | ○ | ○ | ○ | ○ |
| 38 | FSH4 (0.10) | NBDi (0.20) | | 1.62 | 40 | 1.30 | ○ | ○ | ○ | ○ | ○ |
| 39 | FSH4 (0.10) | IPDi (0.10) HDi (0.10) | | 1.60 | 40 | 1.26 | ○ | ○ | ○ | ○ | ○ |
| 40 | FSH4 (0.10) | XDi (0.30) | PET (0.05) | 1.66 | 32 | 1.38 | ○ | ○ | ○ | ○ | ○ |
| 41 | FSH4 (0.10) | HMDi (0.22) | PEMP (0.01) | 1.60 | 42 | 1.24 | ○ | ○ | ○ | ○ | ○ |
| 42 | FSH4 (0.10) | HMDi (0.18) | Cyclohexyl isocyanate (0.04) | 1.60 | 42 | 1.23 | ○ | ○ | ○ | ○ | ○ |
| 43 | FSH4 (0.10) | XDi (0.23) | 1-Thioglycerin (0.02) | 1.65 | 33 | 1.36 | ○ | ○ | ○ | ○ | ○ |
| 44 | FSH4 (0.10) | XDi (0.25) | 1,4-Dithian-2,5-dimercaptomethyl (0.05) | 1.66 | 32 | 1.36 | ○ | ○ | ○ | ○ | ○ |
| 45 | FSH4 (0.10) | Bis(4-isothiocyanatophenyl) sulfide (0.15) | | 1.75 | 20 | 1.38 | ○ | ○ | ○ | ○ | ○ |

TABLE 1-continued

| | | | | | | | | | | |
|---|---|---|---|---|---|---|---|---|---|---|
| 46 | FSH4 (0.10) | XDi (0.05) OCNCH$_2$SSCH$_2$NCS (0.20) | 1.75 | 23 | 1.58 | ○ | ○ | ○ | ○ | ○ |
| 47 | FSH4 (0.10) | XDi (0.19) IPDi (0.09) | 1.66 | 33 | 1.36 | ○ | ○ | ○ | ○ | ○ |

TABLE 2

| Comparative Example | Polythiol (mol) | Isocyanate (mol) | Refractive index | Abbe's number | Specific gravity | Heat resistance | Dye affinity | Impact resistance | Weather-ability | Optical distortion |
|---|---|---|---|---|---|---|---|---|---|---|
| 1 | GST (0.16) | XDi (0.24) | 1.66 | 32 | 1.35 | Δ | ○ | ○ | ○ | ○ |
| 2 | GMT (0.16) | XDi (0.24) | 1.66 | 32 | 1.34 | ○ | ○ | ○ | ○ | ○ |
| 3 | PET (0.7) | XDi (0.34) | 1.66 | 32 | 1.38 | ○ | X | ○ | ○ | ○ |
| 4 | PET (0.15) GST (0.47) | XDi (1.00) | 1.66 | 32 | 1.36 | ○ | ○ | ○ | ○ | ○ |
| 5 | Pentaerythritoltetrakis-thioglycolate (0.10) | XDi (0.20) | 1.60 | 35 | 1.44 | ○ | ○ | ○ | ○ | ○ |
| 6 | Tetrabromobisphenol A (0.20) | XDi (0.20) | 1.61 | 31 | 1.52 | ○ | X | X | X | X |
| 7 | 1,4-Benzenedithiol (0.20) | XDi (0.25) | 1.68 | 28 | 1.36 | ○ | X | X | Δ | ○ |
| 8 | (structure, 0.20) | XDi (0.20) | 1.66 | 30 | 1.34 | ○ | ○ | X | Δ | ○ |
| 9 | (structure, 0.12) | XDi (0.18) | 1.64 | 31 | 1.26 | X | ○ | ○ | ○ | ○ |
| 10 | 1,4-Dithian-2,5-dimer-captomethyl (0.20) | XDi (0.20) | 1.66 | 32 | 1.38 | ○ | X | X | ○ | ○ |

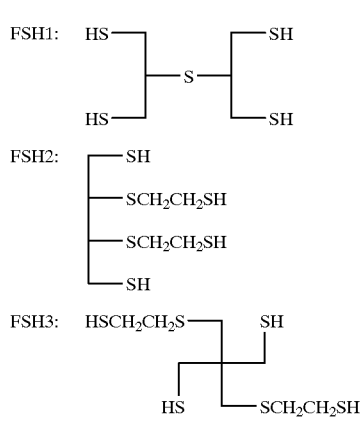

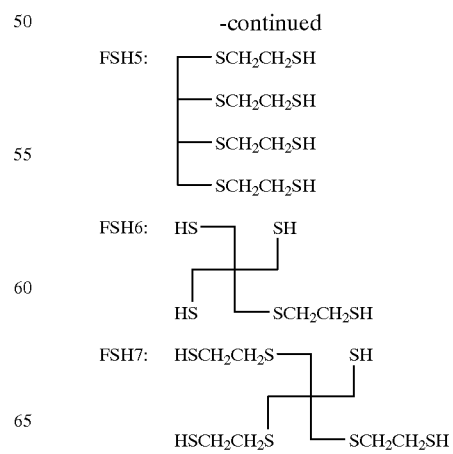

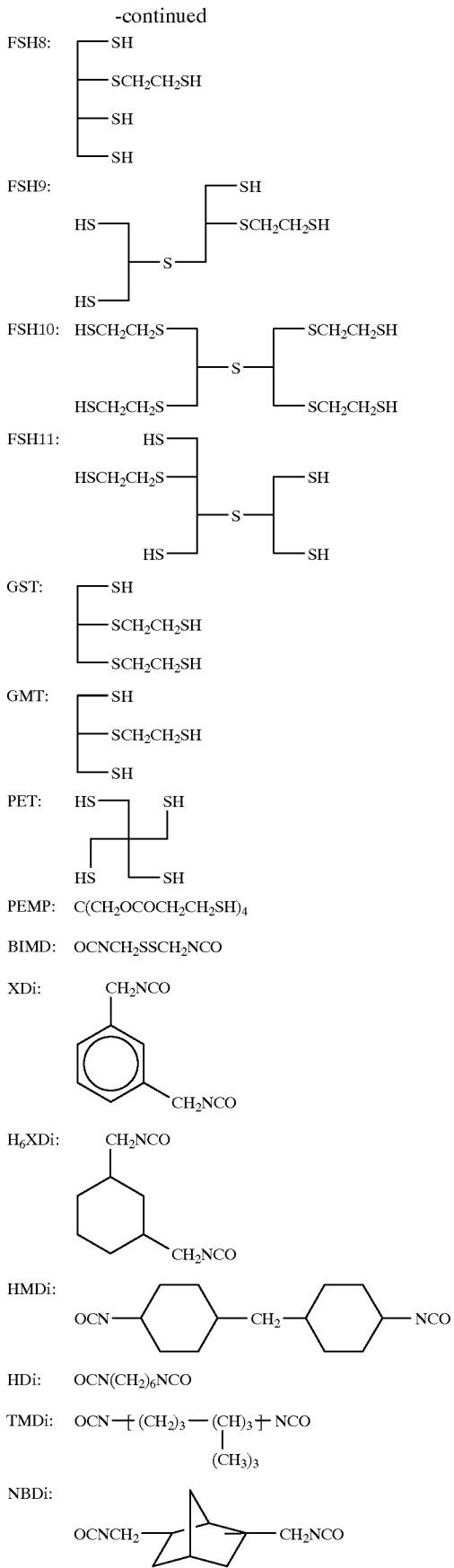

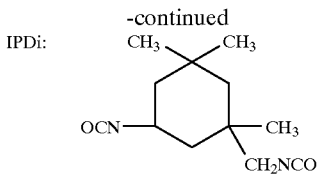

What is claimed is:

1. A sulfur-containing urethane-based resin composition comprising a polythiol having four or more functional groups and at least one isocyanate selected from the group consisting of polyisocyanate compounds, polyisothiocyanate compounds and isocyanato group-containing polyisothiocyanate compounds, said polythiol being represented by any of the following formula (1):

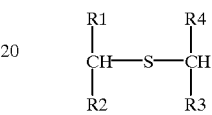

wherein R1, R2, R3 and R4 are each selected from the group consisting of H, —CH$_2$SH, —CH$_2$SCH$_2$CH$_2$SH,

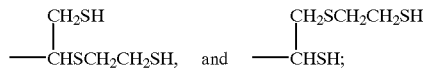

provided that where any one of R1, R2, R3 and R4 is H, at least one of the other three radicals represents

where any two of R1, R2, R3 and R4 are H, two others are independently selected from

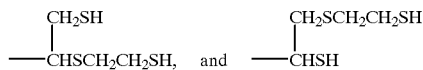

and any three or all of R1, R2, R3 and R4 are not H simultaneously;

formula (2):

wherein m denotes an integer of 1 to 3; and formula (3):

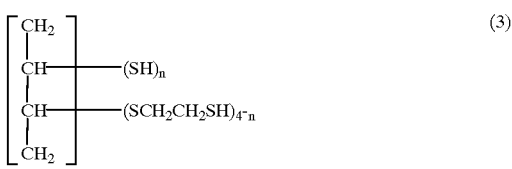

wherein n denotes an integer of 0 to 3.

2. The composition of claim 1 wherein the proportion of the isocyanate to the polythiol is from 0.5 to 3.0 in terms of the molar ratio of the functional groups (NCO+NCS)/SH.

3. The process for producing a sulfur-containing urethane-based resin, which comprises curing the composition of claim 1 by heating.

4. A sulfur-containing urethane-based resin obtained by the process of claim 3.

5. The process of claim 3 wherein the proportion of the isocyanate to the isocyanate to the polythiol is from 0.5 to 3.0 in terms of the molar ratio of the functional groups (NCO+NCS)/SH.

6. A sulfur-containing urethane-based resin obtained by the process of claim 5.

7. The composition of claim 1 wherein the polythiol has the following formula:

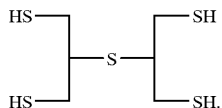

8. The composition of claim 1 wherein the polythiol has the following formula:

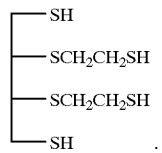

9. The composition of claim 1 wherein the polythiol has the following formula:

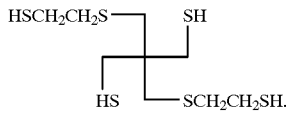

10. The composition of claim 1 wherein the polythiol has the following formula:

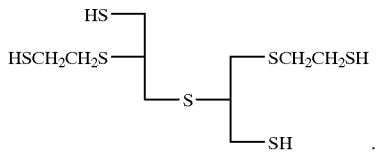

11. The composition of claim 1 wherein the polythiol has the following formula:

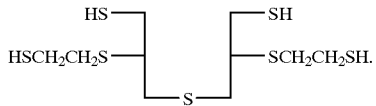

12. The composition of claim 1 wherein the polythiol has the following formula:

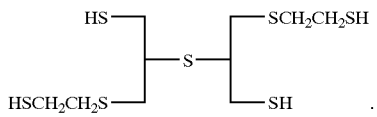

13. The composition of claim 1 wherein the polythiol has the following formula:

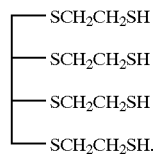

14. The composition of claim 1 wherein the polythiol has the following formula:

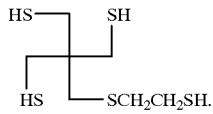

15. The composition of claim 1 wherein the polythiol has the following formula:

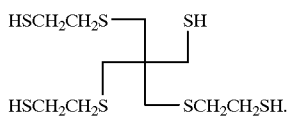

16. The composition of claim 1 wherein the polythiol has the following formula:

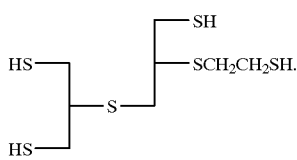

17. The composition of claim 1 wherein the polythiol has the following formula:

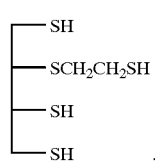

18. The composition of claim 1 wherein the polythiol has the following formula:

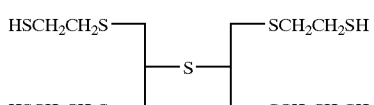

19. The composition of claim 1 wherein the polythiol has the following formula:

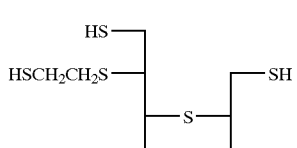

* * * * *